United States Patent
Nakazawa et al.

(10) Patent No.: US 11,065,098 B2
(45) Date of Patent: Jul. 20, 2021

(54) MEDICAL FABRIC

(71) Applicant: Asahi Kasei Kabushiki Kaisha, Tokyo (JP)

(72) Inventors: Akihito Nakazawa, Tokyo (JP); Tokio Okuno, Tokyo (JP)

(73) Assignee: Asahi Kasei Kabushiki Kaisha, Tokyo (JP)

(*) Notice: Subject to any disclaimer, the term of this patent is extended or adjusted under 35 U.S.C. 154(b) by 271 days.

(21) Appl. No.: 16/068,910

(22) PCT Filed: Jan. 18, 2016

(86) PCT No.: PCT/JP2016/051300
§ 371 (c)(1),
(2) Date: Jul. 10, 2018

(87) PCT Pub. No.: WO2017/126009
PCT Pub. Date: Jul. 27, 2017

(65) Prior Publication Data
US 2019/0015192 A1    Jan. 17, 2019

(51) Int. Cl.
*A61F 2/07* (2013.01)
*D03D 3/02* (2006.01)
(Continued)

(52) U.S. Cl.
CPC .............. *A61F 2/07* (2013.01); *D01D 5/088* (2013.01); *D03D 1/00* (2013.01); *D03D 3/02* (2013.01);
(Continued)

(58) Field of Classification Search
CPC .... D03D 13/00; D03D 13/002; D03D 13/004; D03D 13/006; D03D 13/008; D03D 1/00;
(Continued)

(56) References Cited

U.S. PATENT DOCUMENTS 4,870,966 A * 10/1989 Dellon ............... A61B 17/1128
606/152
5,466,514 A    11/1995 Kataoka et al.
(Continued)

FOREIGN PATENT DOCUMENTS

JP    S64-032857 A    2/1989
JP    H08-280816 A    10/1996
(Continued)

OTHER PUBLICATIONS

International Search Report issued in corresponding International Patent Application No. PCT/JP2016/051300 dated Mar. 29, 2016.
(Continued)

*Primary Examiner* — Thomas McEvoy
(74) *Attorney, Agent, or Firm* — Morgan, Lewis & Bockius LLP

(57) ABSTRACT

Provided is a medical fabric that is thin, and has both high tear strength and low water permeability. The medical fabric is characterized in that multifilament yarns having a total fineness of 7-80 dtex are disposed in the warp and weft, the single yarn fineness of at least one of the multifilament yarns among the warp and weft is 0.5 dtex or less, the twist factor A of the weft is 50-2,000, the thickness is 10-90 μm, and the water permeability both before and after puncture by a needle is 300 cc/min/cm² or less.

20 Claims, 7 Drawing Sheets

(51) Int. Cl.
  *D03D 15/33* (2021.01)
  *D01D 5/088* (2006.01)
  *D03D 1/00* (2006.01)
  *D06C 7/02* (2006.01)
  *A61F 2/06* (2013.01)
  *A61F 2/95* (2013.01)

(52) U.S. Cl.
  CPC ............... *D03D 15/33* (2021.01); *D06C 7/02* (2013.01); *A61F 2/95* (2013.01); *A61F 2002/065* (2013.01); *A61F 2240/001* (2013.01); *A61F 2250/0023* (2013.01); *D10B 2331/04* (2013.01); *D10B 2509/06* (2013.01)

(58) Field of Classification Search
  CPC ....... D03D 3/02; A61F 2/07; A61F 2002/065; D10B 2509/06
  See application file for complete search history.

(56) References Cited

U.S. PATENT DOCUMENTS

| | | | |
|---|---|---|---|
| 5,632,763 | A | 5/1997 | Glastra |
| 2007/0293932 | A1* | 12/2007 | Zilla .................... A61B 5/1076 623/1.11 |
| 2009/0171450 | A1 | 7/2009 | Goldmann et al. |
| 2012/0226344 | A1 | 9/2012 | Shirokaze et al. |
| 2013/0041452 | A1 | 2/2013 | Fujita et al. |
| 2015/0081004 | A1 | 3/2015 | Takahashi et al. |
| 2016/0184488 | A1 | 6/2016 | Toyoda et al. |
| 2017/0143872 | A1* | 5/2017 | Limem ................. A61L 15/325 |

FOREIGN PATENT DOCUMENTS

| | | |
|---|---|---|
| JP | H11-302944 A | 11/1999 |
| JP | 2003-183948 A | 7/2003 |
| JP | 2004-115976 A | 4/2004 |
| JP | 2011-229713 A | 11/2011 |
| JP | 2013-515177 A | 5/2013 |
| JP | 2013-158352 A | 8/2013 |
| JP | 2016-014204 A | 1/2016 |
| WO | 94/21848 A1 | 9/1994 |
| WO | 2011/075721 A1 | 6/2011 |
| WO | 2013/137263 A1 | 9/2013 |
| WO | 2015/037671 A1 | 3/2015 |

OTHER PUBLICATIONS

International Preliminary Report on Patentability and Written Opinion issued in corresponding International Patent Application No. PCT/JP2016/051300 dated Aug. 2, 2018.

Office Action issued in corresponding Japanese Patent Application No. 2015-001127 dated Oct. 2, 2018.

Supplemental European Search Report issued in corresponding European Patent Application No. 16886252.2 dated Jan. 11, 2019.

* cited by examiner

MEDICAL FABRIC

FIELD

The present invention relates to a medical fabric suitable as a material for implantation into the human body, which has excellent tear force and low water permeability in spite of being thin and can be suitably used in a stent graft fabric, for example, a graft having a branched (bifurcated) portion for stent grafts.

BACKGROUND

Conventional treatment for aortic aneurysm has included artificial blood vessel replacement using artificial blood vessels. Recently, transcatheter intravascular treatment using stent grafts has fast grown.

This is because the stent graft operation involves neither thoracotomy nor laparotomy and therefore reduces the physical and economical burdens. This stent graft is inserted in a catheter, which is then introduced through the artery at the base of the foot and delivered into an operation site. Therefore, catheters are required to have a low profile, and it is also desired that stent grafts are folded small, because such catheters and stent grafts can be applied even to patients having narrow arteries.

For narrowing stent grafts, it is necessary to reduce the thicknesses of stent graft fabrics. For reducing the thicknesses of stent graft fabrics, it is necessary to reduce the total fineness and single filament fineness of fibers constituting the fabrics, i.e., to use superfine fibers. However, thin fabrics have a high water permeability and increase endoleak. Extremely thin fabrics using superfine fibers have small tear force and may disadvantageously tear from a suture site fitted with a stent.

Patent Document 1 describes a stent graft fabric having better tear force than ever, comprising a fiber having small total fineness and single filament fineness. However, this literature does not state that the narrow fiber is twisted. This approach does not respond to further improvement in tear force.

Patent Document 2 discloses that a woven fabric made of a narrow fiber may comprise yarn produced by twisting individual filaments. This literature states that the yarn twisting is aimed at obtaining large strength, smoothness, and enhanced uniformity. However, all of these purposes are directed to improvement in suitability for weaving steps. The literature does not state that the physical properties of the woven fabric are improved by twist number adjustment. For these reasons, any stent graft fabric having a small thickness, high tear force, and low water permeability has not yet been obtained.

Patent Documents 3-5 disclose a graft having a branched portion. Patent Document 3 discloses the structures of the branched portion sharing individual vascular walls, and cross-link of branches. However, this literature does not show specific woven texture or placement. This approach is difficult to actually utilize. Patent Document 4 discloses a branched graft shape, which relates to opening and closing for blood flow on the lateral side. Patent Document 5 discloses an approach for placing a stent in a branched portion, but does not show the specific woven texture, etc., of the branched portion. Thus, none of the previous literatures suggest an approach effective for the boundary portions of branched grafts. Under these circumstances, there are persistent concerns about leak from the boundary portion of a graft.

The present inventors have prepared models of the branched stent grafts of these conventional techniques and evaluated their characteristics. However, these models have still failed to overcome the problems of leak from the boundary portion of concern. As mentioned above, any medical fabric having a branched portion, which can solve the problems associated with the prevention of leak in medical practice, and low profiles at the same time, has not yet been obtained for medical material grafts for branched stent grafts.

PRIOR ART DOCUMENTS

Patent Documents

Patent Document 1: WO2013/137263
Patent Document 2: National Publication of International Patent Application No. 2013-515177
Patent Document 3: JP-A-64-32857
Patent Document 4: JP-A-2013-158352
Patent Document 5: JP-A-8-280816

SUMMARY

Problems to be Solved by the Invention

An object of the present invention is to provide a stent graft fabric which possesses a small thickness, high tear force, and low water permeation, particularly, to provide a seamless tubular medical fabric for use in a graft for branched stent grafts which allows a material for implantation into the human body to have a low profile and has necessary water permeability and burst strength.

Means for Solving the Problems

The present inventors have conducted diligent studies and experiments and consequently completed the present invention by finding that: the desired low water permeability and tear force can be attained by adjusting the twist coefficient of warp yarn and/or weft yarn; and a graft for branched stent grafts made of a woven fabric with a branched portion having specific woven texture leads to the prevention of leak.

Specifically, the present invention is as described below.

[1] A medical fabric comprising multifilament yarns with a total fineness of 7 to 80 dtex as warp yarns and weft yarns, wherein the single filament fineness of at least one multifilament yarn among the warp yarns and the weft yarns is 0.5 dtex or less, the twist coefficient A of the weft yarns is 50 to 2000, the thickness of the medical fabric is 10 to 90 µm, and the water permeability before and after needle puncture of the medical fabric is 300 cc/min/cm$^2$ or less.

[2] The medical fabric according to [1], wherein the degree of weft yarn overlap (WW) of the weft yarns is 1.0 to 1.5.

[3] The medical fabric according to [1] or [2], wherein the warp yarn crimp angle of the warp yarns is 20 degrees or smaller.

[4] The medical fabric according to any of [1] to [3], wherein intra-yarn single filament fineness ratios S for both the warp yarns and the weft yarns are 2 or less.

[5] The medical fabric according to any of [1] to [4], wherein the warp/weft twist coefficient ratio B between the warp yarns and the weft yarns is 1.5 to 20.

[6] The medical fabric according to any of [1] to [5], wherein the ratio of a diameter in the horizontal direction (Dh) to a diameter in the vertical direction (Dv) in the weft yarn cross section of the woven fabric is 1.5<Dh/Dv<10.

[7] The medical fabric according to any of [1] to [6], wherein the sum of the cover factor (CFw) of the warp yarns and the cover factor (CFf) of the weft yarns (CFw+CFf) is 1600 to 2400.

[8] A tubular seamless fabric comprising a medical fabric according to any of [1] to [7].

[9] The seamless fabric according to [8], wherein the seamless fabric has a large diameter portion and a branched portion, wherein partial fabric texture at the boundary portion between the large diameter portion and the branched portion is constituted by a single texture and has a burst strength of 100 N or larger.

[10] The seamless fabric according to [9], wherein the number of warps constituting the single texture is 2 to 32.

[11] A stent graft comprising a medical fabric according to any of [1] to [7] or a seamless fabric according to any of [8] to [10].

[12] A catheter in which a stent graft according to [11] is inserted.

[13] A stent delivery device comprising a stent graft according to [11] as a component thereof.

[14] A method for producing a seamless fabric according to [9] or [10], comprising the step of performing weaving in a loom provided with a shuttle having a weft yarn wound on a bobbin.

Effects of the Invention

The medical fabric of the present invention has a small thickness, high tear force, and a small water permeability and as such, is most suitable as a high grade stent graft fabric, artificial blood vessel, and the like. The seamless tubular medical fabric according to the present invention has water permeability and burst strength necessary as a material for implantation into the human body, and is useful for a graft for branched stent grafts that can have a low profile and can minimize leak by using specific woven texture in the branched portion.

EMBODIMENTS FOR CARRYING OUT THE INVENTION

Figure 1:
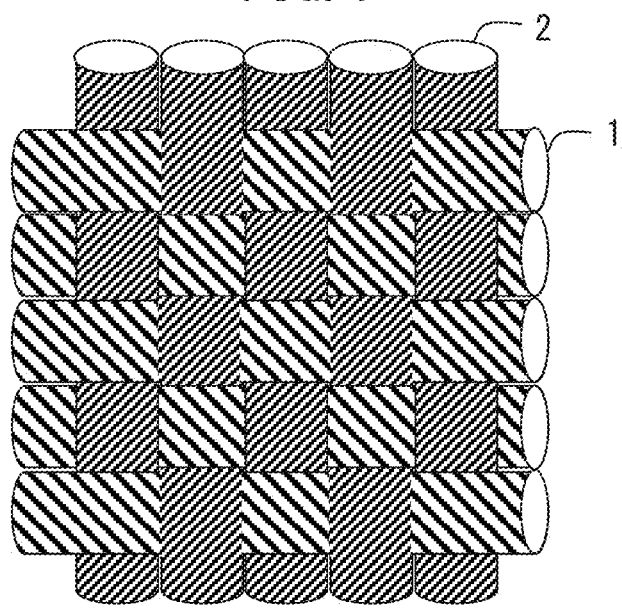
FIG. 1 is a schematic view showing one example of the medical fabric of the present embodiment.

Hereinafter, the medical fabric of the present embodiment will be described in detail.

The medical fabric of the present embodiment is a fabric comprising multifilament yarn with total fineness of 7 to 80 dtex as warp yarn and weft yarn, wherein a specific superfine (ultrafine) fiber is disposed in at least a portion of the warp yarn and the weft yarn. In this context, the total fineness of the warp yarn or the weft yarn is the fineness of the whole yarn constituting the warp yarn or the weft yarn.

The specific superfine fiber is a fiber having single filament fineness of 0.5 dtex or less and total fineness of 7 to 80 dtex. In this context, the total fineness of the superfine fiber is the product of fineness per monofilament constituting the superfine fiber, and a total filament number.

Examples of the superfine fiber used in the medical fabric of the present embodiment include, but are not limited to, fibers of polyester, polypropylene, polyamide, polyurethane, polyethylene terephthalate (PET), polybutylene terephthalate, polycyclohexane terephthalate, and fluorine resins such as PTFE and ETFE. Polyester such as polyethylene terephthalate or a fluorine resin such as PTFE or ETFE is preferred from the viewpoint of high in vivo structural stability, prolonged durability, and good handleability. Polyester such as polyethylene terephthalate or a fluorine resin such as PTFE or ETFE having a glass transition temperature of 50° C. or higher that prevents fiber strength from being reduced due to change in temperature in vivo is more preferred.

One superfine fiber or two or more superfine fibers differing in fiber material or fineness in combination can be used according to a purpose. The combined superfine fibers may be used as a composite fiber comprising the two or more fibers twisted with each other or may be used as separate fibers in the warp yarn and the weft yarn, respectively, of the woven fabric, or may be used partially in certain sections. Examples of the combination include a combination of a superfine polyester fiber and a superfine fiber of a fluorine resin, a combination of a superfine polyester fiber and a polyester fiber having single filament fineness of 0.5 dtex or more, and a combination of a superfine polyester fiber and a fluorine resin fiber having single filament fineness of 0.5 dtex or more.

A multifilament having a filament number of 100 or more is more preferred for reducing water permeability and improving flexibility.

For the medical fabric of the present embodiment, the superfine fiber having single filament fineness of 0.5 dtex or less and total fineness of 7 to 80 dtex needs to be disposed in the warp yarn and/or the weft yarn of the woven fabric. The superfine fiber is preferably used in at least the weft yarn from the viewpoint of flexibility in the width direction and the prevention of wrinkles. The superfine fiber is more preferably disposed in both the warp yarn and the weft yarn of the woven fabric for reducing a water permeability.

The medical fabric of the present embodiment may be made of only the superfine fiber, or a fiber other than the superfine fiber may also be used therewith. The fiber other than the superfine fiber is not particularly limited and can be selected such that the warp yarn and the weft yarn are constituted by multifilaments with total fineness of 7 to 80 dtex. However, a medical fabric having large variation in the intra-yarn single filament fineness of the warp yarn and the weft yarn might not properly exert desired effects. Therefore, the intra-yarn single filament fineness ratios S of the warp yarn and the weft yarn are preferably 2 or less, more preferably 1.5 or less, further preferably 1.3 or less. The intra-yarn single filament fineness ratio S of 2 or less is desirable because gaps between monofilaments are decreased and a water permeability before and after needle puncture can be reduced. In this context, the intra-yarn single filament fineness ratio S is the fineness ratio between a monofilament having the largest fineness and a monofilament having the smallest fineness among filaments constituting the warp yarn or the weft yarn and can be calculated from the ratio between a monofilament having the largest weight and a monofilament having the smallest weight among monofilaments extracted from yarn of a given length.

In the medical fabric of the present embodiment, the warp yarn and the weft yarn are preferably selected such that the warp/weft yarn single filament fineness ratio of the single filament fineness Dw (dtex) of the warp yarn to the single filament fineness Df (dtex) of the weft yarn is 2≤Dw/Df≤20, more preferably 5≤Dw/Df≤20, further preferably 10≤Dw/Df≤20. The warp yarn and the weft yarn differing in single filament cross sectional diameter by Dw/Df of 2 or more are desirable for the following reasons: in a stent graft, blood usually flows warpwise so that the warp yarn is placed under large tensile load. Therefore, it is preferred to enhance tensile strength warpwise by increasing the single filament fineness of the warp yarn over that of the weft yarn. Also, the single filament fineness of the weft yarn smaller than that of the warp yarn is preferred because flexibility is enhanced to facilitate deformation and resist wrinkles. The Dw/Df of 20 or less is desirable because the crimp percentage of the weft yarn is kept low and a water permeability can be reduced. Each of Dw and Df is the average single filament fineness of filaments constituting each yarn.

The total fineness of the warp yarn and the weft yarn constituting the medical fabric of the present embodiment needs to be 7 dtex or more and 80 dtex or less for the reduced thickness of a stent graft fabric and no generation of the problems of fluff or yarn breakage during weaving. A high density woven fabric can be produced by adjusting the total fineness to 80 dtex or less. When the warp yarn or the weft yarn is made of only the superfine fiber, the total fineness of the superfine fiber is 7 dtex or more and 80 dtex or less.

If the total fineness of the warp yarn and the weft yarn constituting the medical fabric of the present embodiment is less than 7 dtex, the thickness of the resulting fabric is reduced to a suitable low profile required for a stent graft. However, this fabric has reduced tear force or poor passage through the processing steps in such a way as to frequently suffer fluff or yarn breakage during the molding process including the weaving process. If the total fineness of the superfine fiber exceeds 80 dtex, the thickness of the resulting fabric exceeds 90 μm even if the single filament fineness is 0.5 dtex or less. This fabric is not able to pass through a 6 mm diameter hole (assuming a 6 mm inner diameter catheter), when prepared into a tubular fabric with an inner diameter of 50 mm, for example. The total fineness of the superfine fiber is preferably 10 dtex or more and 70 dtex or less, more preferably 15 dtex or more and 60 dtex or less, further preferably 20 dtex or more and 50 dtex or less, from the viewpoint of achieving both the reduced thickness and high tear force of the fabric.

On the other hand, the single filament fineness of the superfine fiber is preferably 0.5 dtex or less. In this context, the single filament fineness is fineness per monofilament. When the single filament fineness is 0.5 dtex or less, the increased affinity for vascular endothelial cells promotes integration between the vascular wall tissue and the woven fabric, thus helping to prevent movement and separation of the stent graft inside the vessel and to suppress the formation of blood clots. The single filament fineness of the fiber is preferably 0.4 dtex or less, more preferably 0.3 dtex or less, from the viewpoint of the reduced thickness of the woven fabric and the affinity for cells. The lower limit of the single filament fineness is not particularly limited and is preferably 0.01 dtex or more, more preferably 0.03 dtex or more, from the viewpoint of passage through the warping step in the woven fabric production process, the weaving steps, or the like, and the exertion of the burst strength of the woven fabric.

The weft yarn constituting the medical fabric of the present embodiment needs to be twisted according to the fineness such that the twist coefficient A is 50 to 2000, preferably 50 to 1500, more preferably 50 to 1000, further preferably 50 to 800. The twist coefficient of 50 or more improves the bundling property of the weft yarn and improves the tear resistance of the yarn itself. In addition, rounded and slidable yarn gathers many wefts during tear and improves tear force. Furthermore, the problems of fluff or yarn breakage during weaving are decreased, leading to improvement in process stability. The twist coefficient of 2000 or less easily flattens the weft yarn on the woven fabric, decreases gaps between adjacent wefts, and can reduce a water permeability.

It is preferred that in addition to the weft yarn, the warp yarn should be twisted according to the fineness such that the twist coefficient is 75 to 10000. During weaving, the warp yarn is placed under large load such as yarn-on-yarn abrasion, yarn-to-metal friction, tension, or bending. Therefore, it is preferred to improve rub resistance by using twisted warp yarn. Since the superfine fiber has small single filament fineness and is therefore susceptible to fluff or yarn breakage during weaving, it is more preferred to improve process stability by twisting.

In this context, the twist coefficient is a value calculated according to the following expression:

$$\text{Twist coefficient} = T \times (D)^{1/2}$$

wherein T represents the twist number (T/m) of twisted yarn, and D represents the total fineness (dtex) of the twisted yarn.

The cross sectional shape of the fiber used in the warp yarn and the weft yarn is not particularly limited and can assume a round cross section, a triangle cross section, a multi-lobate cross section, a hollow cross section, a flat cross section, a segmented core-clad cross section, or the like.

The twisted yarn can also be used as a composite fiber in which two or more fibers differing in fiber material or fineness are twisted with each other. Alternatively, each of the weft yarn and the warp yarn used may have a distinctive twist number of twisted yarn. The weft yarn and the warp yarn are preferably twisted in the same direction. This is preferred because the weft yarn and the warp yarn twisted in the same direction come in closer contact with each other and can reduce a water permeability while the resulting woven fabric is thin.

The twisted yarn constituting the woven fabric of the present embodiment can be subjected to twist setting, if necessary. In this case, the setting conditions for the twisted yarn preferably involve vacuum steam setting at 70° C. for 30 minutes.

In the medical fabric of the present embodiment, the tear force of the woven fabric in the single tongue method is not particularly limited and is preferably 3 N or larger, more preferably 3.5 N or larger, further preferably 4 N or larger, in both the warp and weft directions. Also, the tear force of the woven fabric is preferably 20 N or smaller. When the tear force of the woven fabric falls within the range described above, the resulting woven fabric is lightweight and thin and has necessary tear force. On the other hand, if the tear force is smaller than 3 N, the possibility of tear from a suture site is increased. Tear force exceeding 20 N is not preferred because the fineness needs to be increased, thereby rendering the fabric thick and hard.

In the medical fabric of the present embodiment, the warp yarn is preferably hardened over the weft yarn during weaving.

The warp yarn and the weft yarn differing in hardness are desirable for the following reasons.

In the medical fabric of the present embodiment, the weft yarn needs to be twisted for improving tear force. The twisting rounds the yarn shape and expands gaps between adjacent wefts, thereby deteriorating water permeability. Furthermore, the thickness is not reduced because the yarn is not flattened. This problem becomes apparent, particularly, when the superfine fiber is disposed in the weft yarn and twisted.

In order to overcome this problem, it is desirable to harden the warp yarn over the weft yarn during weaving, thereby flattening the twisted weft yarn by the force of the warp yarn and decreasing the gaps between adjacent wefts. One example of the hardening method includes, but is not particularly limited to, a method which involves adjusting the twist coefficient of the warp yarn to higher than the twist coefficient of the weft yarn. The warp/weft twist coefficient ratio B (B=Twist coefficient of the warp yarn/Twist coefficient of the weft yarn) is preferably 1.5 to 20. When the warp/weft twist coefficient ratio B is 1.5 or more, the warp yarn can be harder than the weft yarn. Thus, the twisted weft yarn of the superfine fiber is flattened by the force of the warp yarn, and the gaps between adjacent wefts are decreased. When the warp/weft twist coefficient ratio B is 20 or less, the warp yarn does not have an excessive twist number and decreases gaps between adjacent warps. As another example, it is preferred to adjust warp yarn tension to higher than weft yarn tension (warp yarn tension>weft yarn tension) during weaving. Since the superfine fiber is used in the weft yarn, the weft yarn tension is preferably 0.2 cN/dtex or smaller. The warp yarn tension is preferably 0.3 to 1.5 cN/dtex, more preferably 0.4 to 1.0 cN/dtex, further preferably 0.5 to 0.9 cN/dtex. When the warp yarn tension is 0.3 cN/dtex or larger, the picking property of the weft yarn is improved during weft picking. When the warp yarn tension is 1.5 cN/dtex or smaller, stable weaving can be achieved without yarn breakage and fluff. An alternative method involves hardening only the warp yarn over the weft yarn by sizing only the warp yarn without sizing the weft yarn. A further alternative method preferably involves adjusting the warp/weft total fineness ratio (total fineness of the warp yarn/total fineness of the weft yarn) to 1 to 10. When the warp/weft total fineness ratio is 1 or more, only the warp yarn can be harder than the weft yarn. When the warp/weft total fineness ratio is 10 or less, the thickness can be reduced. The warp yarn and the weft yarn are preferably selected such that the warp/weft single filament fineness ratio Dw/Df is $2 \leq Dw/Df \leq 20$, more preferably $5 \leq Dw/Df \leq 20$, further preferably $10 \leq Dw/Df \leq 20$. Dw/Df of 2 or more is preferred because only the warp yarn can be harder than the weft yarn. Also, Dw/Df of 20 or less is desirable because the crimp percentage of the weft yarn is kept low and a water permeability can be reduced. Each of Dw and Df is the average single filament fineness of filaments constituting each yarn. Also, the number of monofilaments is more preferably larger in the weft yarn than in the warp yarn (the number of monofilaments of the weft yarn>the number of monofilaments of the warp yarn). Thus, the reduced thickness, high tear force, and low water permeation of interest can be attained by hardening the warp yarn over the weft yarn.

The filaments of the warp yarn and/or the weft yarn used in the medical fabric of the present embodiment are preferably coated with a sizing agent before weaving. This can prevent fluff and yarn breakage during weaving and can improve tear force. One example of the sizing method includes a method which involves dipping the yarn in a sizing agent, followed by drying. Examples of the sizing agent include poval sizing agents and acrylic sizing agents. Two or more sizing agents may be used in combination. Components such as a lubricating agent and an antistatic agent may be further added thereto. The sizing agent is preferably a poval sizing agent and an acrylic sizing agent in combination from the viewpoint of resistance to the removal of the sizing agent. Also preferably, no sizing agent is used from the viewpoint of biological safety. The weft yarn of the superfine fiber can be flattened by sizing only the warp yarn without sizing the weft yarn, resulting in improvement in low water permeability, tear force, and reduced thickness.

The woven fabric structure of the medical fabric of the present embodiment is not particularly limited and is plain weave, twill weave, satin weave, crepe weave, or the like. A plain weave structure is preferred from the viewpoint of the reduced thickness of the fabric. An exemplary medical fabric having a plain weave structure is shown in FIG. 1. A ripstop taffeta or double ripstop fabric having ripstop texture can also be used for further enhancing tear force. After weaving, the fabric is subjected to scouring and heat setting, if necessary.

In order to use the medical fabric of the present embodiment as a graft for stent grafts, it is possible to prepare a sheet-like woven fabric or film into a tubular form and bond the ends together using an adhesive or seam the ends together by sewing. However, the bonded or sewn portion has an increased thickness. Thus, the resulting stent graft is not able to be folded small. Therefore, a seamless fabric (woven fabric) is preferred for a low profile. The seamless fabric (woven fabric), which is constituted by continuous weft yarn, can eliminate the complicated bonding or sewing step that varies depending on manual procedures in the case of using a plane (non-tubular) woven fabric or film material, and can reduce leak. Furthermore, the seamless fabric is also effective for smooth blood flow by eliminating surface asperities.

Each of the warp and weft densities of the woven fabric of the present embodiment is preferably 100/2.54 cm or higher, more preferably 120/2.54 cm or higher. The upper limit is not particularly limited and is substantially 300/2.54 cm or lower for weaving.

The degree of weft yarn overlap (WW) of the medical fabric of the present embodiment is preferably 1.0 to 1.5. When the degree of weft yarn overlap (WW) is 1.0 or more, the gaps between adjacent wefts are decreased and a water permeability can be reduced. Also, the degree of weft yarn overlap (WW) of 1.5 or less is desirable because the degree of warp yarn overlap (TT) can also decrease gaps between adjacent warps and reduces a water permeability. The degree of weft yarn overlap (WW) is more preferably 1.1 or more. The degree of warp yarn overlap (TT) is preferably 0.9 or more, more preferably 1.0 or more.

The method for adjusting the degree of weft yarn overlap (WW) to 1.0 or more is not particularly limited and can be achieved by use of the aforementioned configuration in which the warp yarn is hardened over the weft yarn. Another example thereof includes a method which involves using the superfine fiber in the weft yarn and adjusting filling pick count and warp yarn tension. Use of the superfine fiber easily flattens the yarn and improves the degree of weft yarn overlap.

Figure 4:
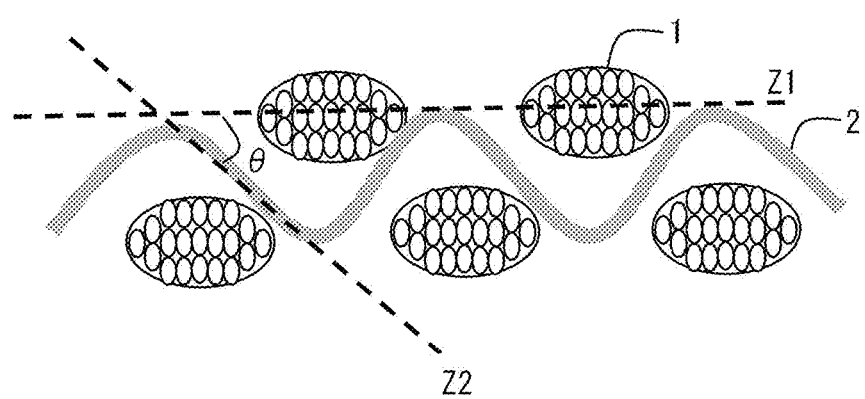
FIG. 4 is a cross-sectional schematic view illustrating a warp yarn crimp angle.

The warp yarn crimp angle of the medical fabric of the present embodiment is preferably 20 degrees or smaller, more preferably 15 degrees or smaller, further preferably 10 degrees or smaller (the warp yarn crimp angle is shown in FIG. 4). The warp yarn crimp angle becomes 20 degrees or smaller by hardening the warp yarn over the weft yarn during weaving. This easily flattens the yarn and improves the degree of weft yarn overlap. The method for adjusting the warp yarn crimp angle to 20 degrees or smaller is not particularly limited and can be achieved by use of the aforementioned configuration in which the warp yarn is hardened over the weft yarn. Particularly, warp yarn tension adjustment is effective. The warp yarn tension is adjusted to the appropriate range as described above so that the warp yarn crimp angle is 20 degrees or smaller and the degree of weft yarn overlap is 0.9 or more. An alternative method involves adjusting the twist coefficient of the warp yarn to higher than the twist coefficient of the weft yarn as described above. As mentioned above, the warp yarn crimp angle becomes 20 degrees or smaller by hardening the warp yarn over the weft yarn. Thus, the reduced thickness, high tear force, and low water permeation of interest can be attained.

In the medical fabric of the present embodiment, the ratio of a diameter in the horizontal direction (Dh) to a diameter in the vertical direction (Dv) on the weft yarn cross section of the woven fabric is preferably 1.5<Dh/Dv<10, more preferably 2<Dh/Dv<10, further preferably 2.5<Dh/Dv<10. The ratio of a diameter in the horizontal direction (Dh) to a diameter in the vertical direction (Dv) on the cross section of the woven fabric is preferably 1.5<Dh/Dv<10 for both the warp yarn and the weft yarn, because a water permeability is reduced. Dh/Dv exceeding 1.5 can flatten the yarn, decrease gaps between adjacent wefts and/or between adjacent warps, and reduce a water permeability. Dh/Dv less than 10 does not reduce the thickness of the yarn too much and can prevent deterioration in water permeability and tear force. Twisted yarn tends to have Dh/Dv less than 1.5 as compared with non-twisted yarn. Therefore, it is more preferred that the twisted yarn should satisfy 1.5<Dh/Dv<10. For reducing a water permeability, it is more preferred that both the warp yarn and the weft yarn should satisfy 1.5<Dh/Dv<10.

In the medical fabric of the present embodiment, the cover factor (CFf) of the weft yarn is preferably 800 or more. CFf can be adjusted by the speed of a surface roll. When the cover factor of the weft yarn is 800 or more, both of the weft density and the degree of weft yarn overlap can be improved.

The cover factor of the weft yarn is calculated according to the following expression:

$$CFf = W^{1/2} \times NW$$

wherein W represents the total fineness (dtex) of the weft yarn extracted from the woven fabric, and NW represents the number of wefts per 2.54 cm long woven fabric (the number of wefts/2.54 cm)}.

The medical fabric of the present embodiment is preferably a high density woven fabric in which the sum of the cover factor (CFw) of the warp yarn and the cover factor (CFf) of the weft yarn is preferably CFw+CFf=1600 to 2400, more preferably CFw+CFf=1700 to 2300, further preferably CFw+CFf=1800 to 2200. CFw, as with CFf, can be calculated from the total fineness of the warp yarn extracted from the woven fabric, and the number of warps (the number of warps/2.54 cm). When the sum of CFw and CFf is 1600 or more, the gaps between adjacent wefts and/or between adjacent warps are decreased and a water permeability can be reduced. When the sum of CFw and CFf is 2400 or less, the resulting fabric is unlikely to have paper-like texture, can prevent rapid reduction in tear force, and keeps its flexibility. Therefore, CF is preferably 2400 or less for obtaining flexible textile having excellent tear force.

Warp-to-warp friction can be prevented during weaving, and production stability can be maintained. In addition, excellent tear force is obtained because of uniform yarn arrangement. For adjusting the degree of warp yarn overlap (TT) and the degree of weft yarn overlap (WW) to 0.9 or more, each of CFw and CFf is more preferably 800 or more from the viewpoint of a low water permeability.

The thickness of the medical fabric of the present embodiment is 10 μm or larger and 90 μm or smaller, preferably 15 μm or larger and 80 μm or smaller, more preferably 20 μm or larger and 70 μm or smaller, from the viewpoint of a low profile. If the thickness of the fabric exceeds 90 μm, the resulting fabric is not able to pass through a 6 mm diameter hole (assuming a catheter), when prepared into a tubular fabric with an inner diameter of 50 mm, for example. On the other hand, if the thickness of the fabric is smaller than 10 μm, adequate tear force or burst strength cannot be retained.

When the medical fabric of the present embodiment is a seamless tubular knitted fabric, its outer diameter depends on the inner diameter of a blood vessel in which the stent graft is used, and is generally 3 mm or larger and 50 mm or smaller, though the outer diameter is not necessarily limited to this range.

In this context, the thickness of the woven fabric is defined as the average of thicknesses measured with a thickness gauge at ten positions arbitrarily selected within a range in the circumferential direction and the length direction (5 cm to 30 cm) of the tubular fabric. In the thickness measurement of the woven fabric, thickness variation Z at each measurement position represented by the following expression:

$$Z(\%) = (Zav - Zi)/Zav \times 100$$

wherein Zav represents the average of the 10 measurement values, Zi represents the measurement value at each position, and i represents an integer of 1 to 10 is preferably within ±15%.

If the thickness variation is negatively large to exceed −15%, the resulting fabric cannot be accommodated in a desired catheter having, for example, a 6 mm diameter hole even if the average thickness of the folded woven fabric is 90 μm or smaller. Also, sections with thickness variation exceeding 15% have a small thickness and impair burst strength and water permeation prevention. The thickness variation Z is more preferably within ±12%, further preferably within ±10%.

For the medical fabric of the present embodiment, the water permeability before and after needle puncture needs to be 300 cc/cm$^2$/min or less. The water permeability of the fabric serves as an index of endoleak prevention. When the water permeability is 300 cc/cm$^2$/min or less, endoleak from the fabric wall face is suppressed. On the other hand, the stent graft fabric is prepared as a final stent graft product sewn together with a metal stent using suture thread. If large needle holes are opened in the fabric during such a procedure, endoleak may occur at those locations. In other words, the water permeability after puncture of a needle also needs to be 300 cc/cm$^2$/min or less for the practical performance of the stent graft fabric. In this context, the water permeability after needle puncture is a value measured after arbitrary passing of a tapered 3/8 needle 10 times through the fabric in a 1 cm$^2$ area. In the tubular seamless fabric of the present embodiment, the monofilaments are pressed flat in the woven texture to fill the gaps at the crossing points of the warp yarn and the weft yarn. Thus, the water permeability before needle puncture is minimized. The water permeability before and after needle puncture of the medical fabric of the present embodiment is preferably 250 cc/cm$^2$/min or less, more preferably 200 cc/cm$^2$/min or less, from the viewpoint of practical performance.

The medical fabric of the present embodiment preferably has burst strength of 100 N or larger at any site measured according to a burst strength test based on ANSI/AAMI/ISO7198: 1998/2001. The burst strength tends to be decreased, particularly, at the boundary portion between branches, but becomes 100 N or larger by constituting the fabric texture by a single texture. If the burst strength of the woven fabric is smaller than 100 N, the resulting woven fabric may present safety problems, when used as a stent graft fabric, in such a way as to burst by the expanding force of the stent. The burst strength is preferably 120 N or larger, more preferably 140 N or larger. The upper limit of the burst strength of the woven fabric is not particularly limited and is substantially 500 N or smaller from the viewpoint of balance with thinness of the woven fabric.

The porosity on the cross sections of the warp yarn and the weft yarn constituting the medical fabric of the present embodiment is preferably 10% or more and 70% or less. The formation of spaces in 10% or more of the woven fabric facilitates infiltration of cells between the monofilaments of the fiber and increases integratability between the vascular wall tissue and the woven fabric (exhibiting an effect of preventing endoleak and preventing movement of the stent graft), while allowing the aforementioned water permeability after needle puncture to be controlled to 300 cc/cm$^2$/min or less. On the other hand, a woven fabric porosity exceeding 70% leads to deformation of the woven fabric and is responsible for increased water permeability. The porosity of the medical fabric of the present embodiment is more preferably 15% or more and 60% or less, still more preferably 20% or more and 50% or less. The porosity may be larger with decrease in single filament fineness.

The crimp percentage of the weft yarn extracted from the medical fabric of the present embodiment is preferably 4% or more and 20% or less. When the crimp percentage is 4% to 20%, the resulting fabric exhibits increased flexibility and has a favorable shape following property within a blood vessel as well as favorable burst strength, small water permeability, etc. If the crimp percentage is smaller than 4%, the resulting fabric has poor flexibility. Therefore, endoleak occurs easily. If the crimp percentage exceeds 20%, the thickness of the woven fabric tends to be increased and may not be suitable for a low profile. The crimp percentage is more preferably 6% or more and 18% or less, still more preferably 8% or more and 15% or less.

Likewise, the crimp percentage of the warp yarn extracted from the medical fabric of the present embodiment is preferably 0.2% or more and 5% or less. When the crimp percentage is 0.2% to 5%, the woven fabric structure is tough warpwise and resists bending or kink of the graft. If the crimp percentage is smaller than 0.2%, poor inflection balance between the warp yarn and the weft yarn tends to deteriorate burst strength and water permeability after needle puncture. Furthermore, the weft yarn is more slidable on the warp yarn so that shift of the yarn occurs, resulting in endoleak. If the crimp percentage exceeds 5%, the rigidity in the vertical direction of the woven fabric tends to be decreased and becomes unsuitable for stability against beating. The crimp percentage is more preferably 0.3% or more and 3% or less, still more preferably 0.4% or more and 2.5% or less.

The tubular seamless fabric of the present embodiment may be coated with an antithrombotic material, collagen, gelatin, heparin, acetylsalicylic acid, polyurethane, or the like, without departing from the requirements such as the desired thickness and outer diameter. Particularly, collagen or gelatin has excellent biocompatibility and low antigenicity and is therefore more preferred. The coating can reduce water permeability and can suppress endoleak.

The tubular seamless fabric of the present embodiment may be hydrophilically coated. The hydrophilization facilitates adsorption of cells and exerts excellent biocompatibility. In addition, the hydrophilization can be expected to be effective for suppressing endoleak. Examples of the hydrophilizing agent include, but are not particularly limited to, polyethylene oxide and polyvinyl alcohol.

The tubular seamless fabric of the present embodiment may be pressed by calendaring or the like. The press working improves the flatness of the weft yarn and the warp yarn and decreases yarn-yarn gaps, thus helping to obtain a low water permeability. The calendaring treatment is preferably performed only on one side of the woven fabric. Calendaring treatment on both sides is not preferred because tear strength is easily reduced. The tubular seamless fabric can be spirally crimped. The crimping treatment prevents crushing (luminal obstruction) caused by kink in the body. Therefore, the crimping treatment is an effective method.

Figure 5:
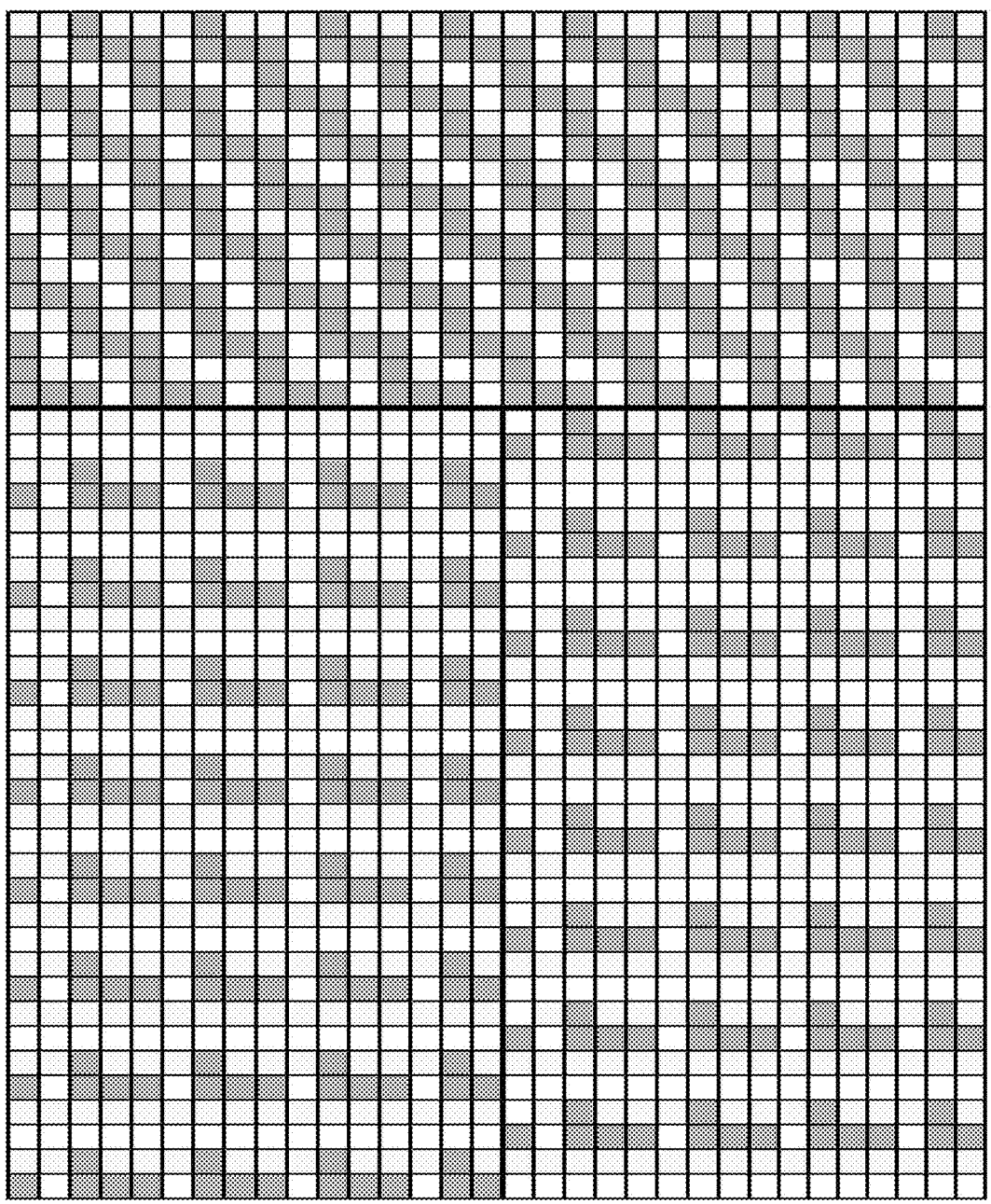
FIG. 5 shows fabric texture in which a single texture is formed neither in a large diameter portion nor in a branched portion.
Figure 6:
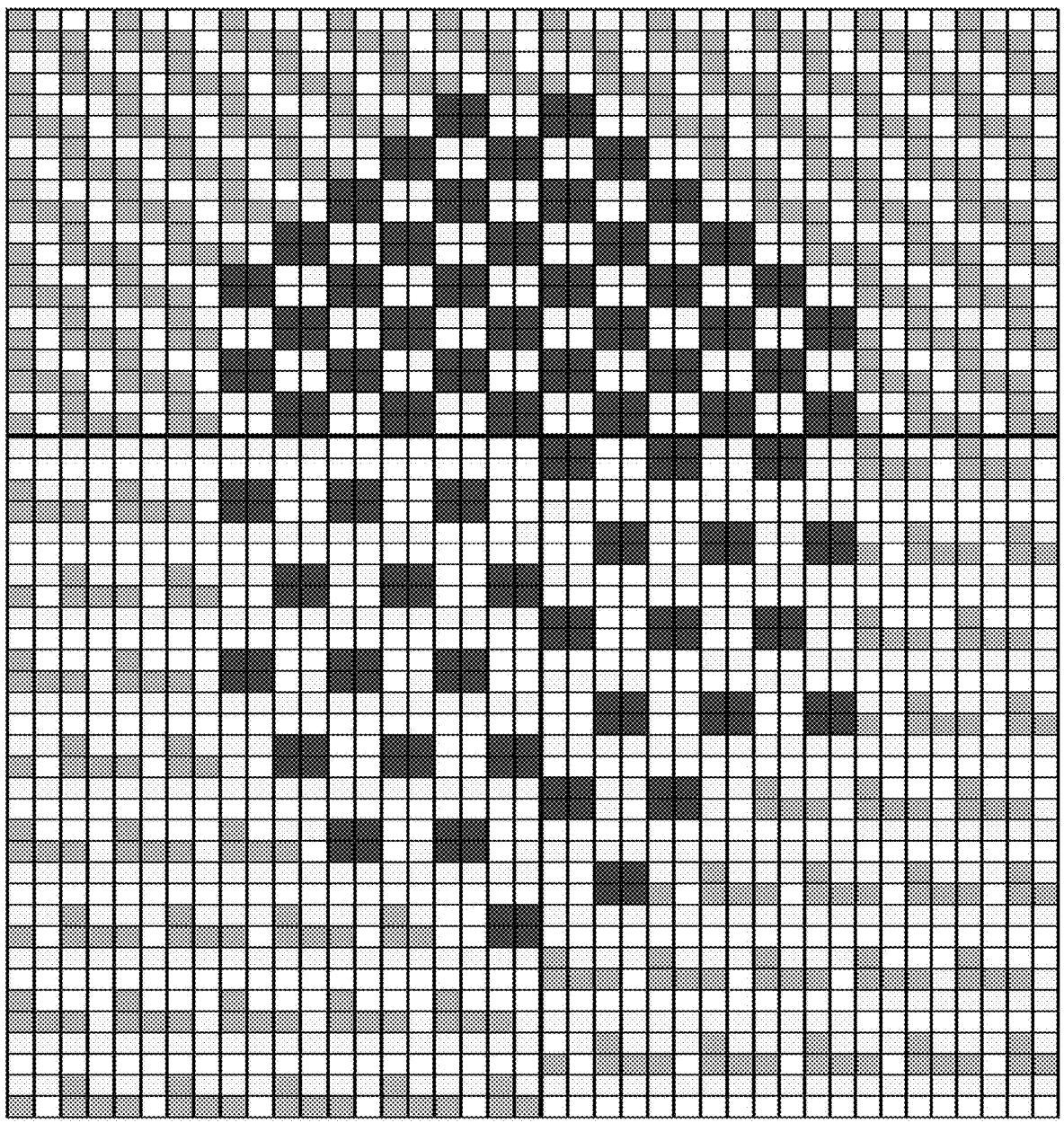
FIG. 6 shows fabric texture in which a single texture is formed both in a large diameter portion and in a branched portion.
Figure 7:
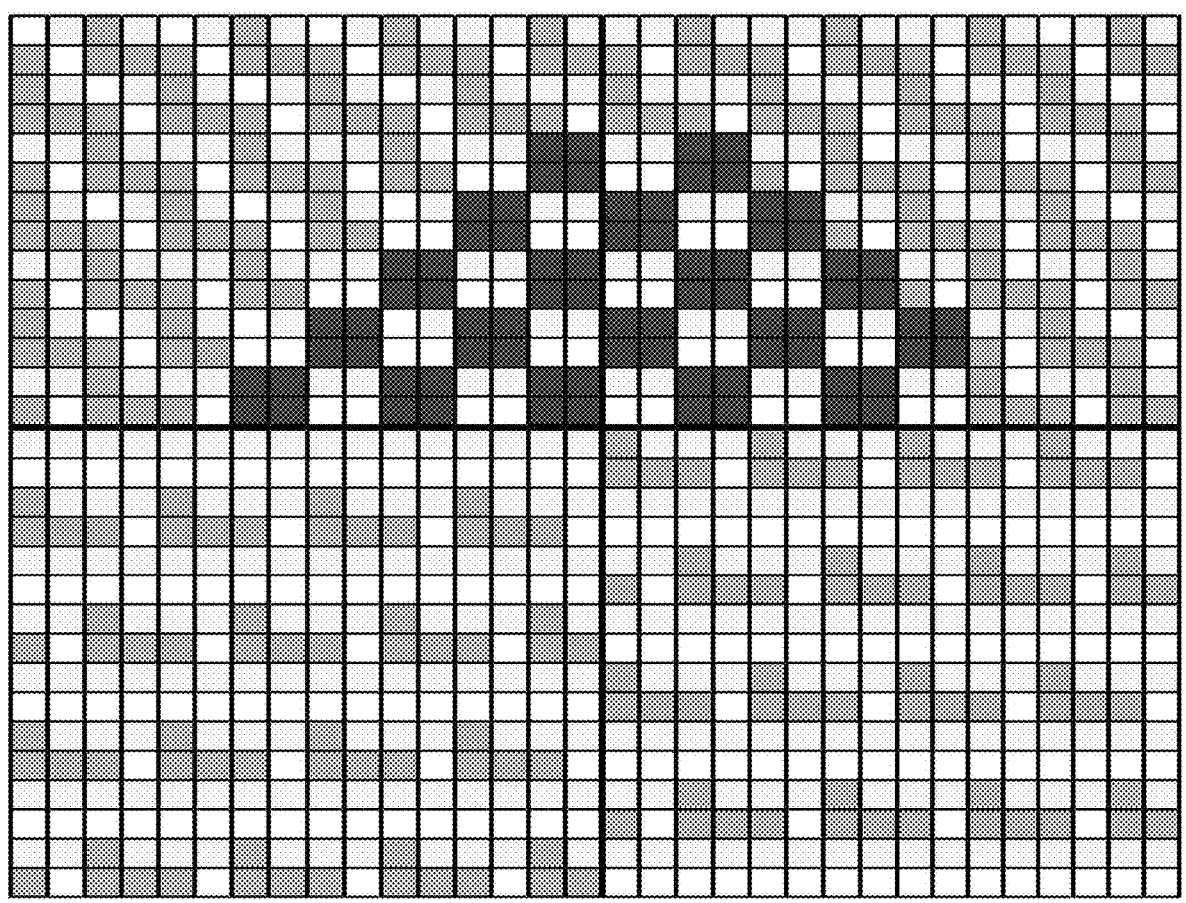
FIG. 7 shows fabric texture in which a single texture is formed only in a large diameter portion.
Figure 8:
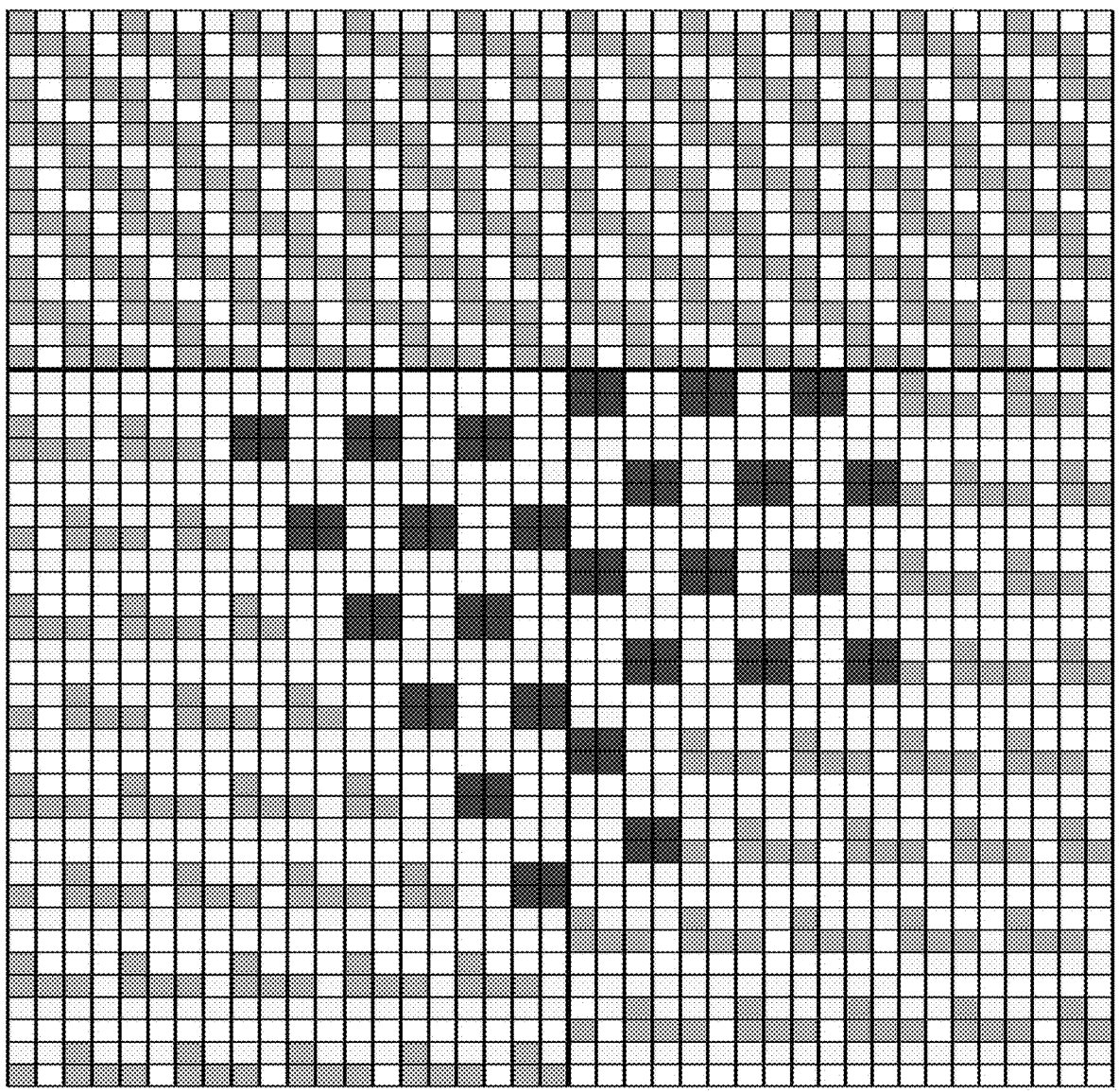
FIG. 8 shows fabric texture in which a single texture is formed only in a branched portion.

The branched portion of the medical fabric of the present embodiment is a portion having two or more branches continuously emanating from a tubular large diameter portion. Partial fabric texture at the boundary portion between the large diameter portion and the branched portion is preferably a single texture. For example, the woven texture constituting a woven fabric with a branched portion having two branches emanating from the large diameter portion is shown in FIG. 5. As shown in FIG. 6, the woven fabric can have a structure where a single texture is disposed in both the large diameter portion and the branched portion. As shown in FIG. 7, the woven fabric may have a structure where a single texture is disposed only in the large diameter portion. The single texture may be disposed only in the branched portion as shown in FIG. 8, but is preferably disposed in both the large diameter portion and the branched portion as shown in FIG. 6.

The single texture can be any structure that connects the upper and lower woven fabrics. For example, 2/2 basket texture, 2/2 twill texture, 3/3 basket texture, or 3/3 woven texture can be used as texture acceptable for the woven structure. Also, 1/2 rib, 2/1 rib, or plain woven texture may be used. The texture can be selected without problems associated with weaving or handling.

The branches in the branched portion of the medical fabric of the present embodiment may differ in their diameters, or may be three or more branches. The branches in the branched portion may have the same length. In general, one of the branches is longer than the other. This is because, for example, in abdominal aneurysm treatment, a catheter having a stent graft with a longer branch compressively inserted therein is introduced through the iliac artery on one side so that the stent graft is indwelled in the aneurysm and then connected with a stent graft with a shorter branch inserted from the other iliac artery.

The number of warps constituting the single texture is preferably 2 to 32. The single texture is preferably present in each branch of the branched portion and more preferably present according to the size of each branch of the branched portion, rather than accumulating to one of a plurality of branches. If the number of warps constituting the single texture is less than 2, any branch present in the branched portion has one warp. The resulting single texture has weak inter-yarn constraint and fails to reduce leak. If the number of warps exceeds 32, the proportion of the single texture portion is increased to decrease the tube diameter near the branched portion and inhibit smooth blood flow. The proportion of the single texture portion more than necessary does not largely change the effects of the single texture. The number of warps is preferably 4 to 16. This reduces leak and is less likely to inhibit blood flow.

The number of wefts constituting the single texture can be the same with the number of warps without particular limitations.

In weaving for the woven fabric of the branched portion of the present embodiment, for example, when one branch is woven, the warp yarn constituting the other branch may be on standby at the upper opening or may be on standby at the lower opening. The woven texture may be produced in an easy-to-weave pattern. There are no particular limitations on, for example, a graft base fabric, which has a small number of warps and places small load on Jacquard machines or dobby machines. In weaving for the woven fabric having the branched portion of the present embodiment, shuttles are preferably prepared according to the number of branches of the branched portion plus the large diameter portion. For example, in the case of weaving the branched portion having two branches, it is preferred to prepare three shuttles accommodating the weft yarn. However, the shuttle used to weave the large diameter portion may be used to weave any branch. Hence, two shuttles are also possible for the weaving.

The tubular seamless fabric of the present embodiment can be used as a stent graft by combination with a stent (spring-like metal) serving as an inflatable member. Examples of the type of the stent graft include a tubular simple straight type, a branched type and a fenestrated type suitable for branched blood vessels, a tapered type that may be combined with the branched type, a deformable bellows type, and a bowed type for the thoracic aorta. The type of the stent graft can be selected according to the state or shape of the affected area.

The material for the stent can be appropriately selected from conventionally known members, and used. Examples of the known members include, but are not particularly limited to, self-inflating materials using shape memory alloys, superelastic metals, or synthetic polymer materials. Examples of metal alloys include nickel-titanium alloy (nitinol), cobalt-chromium-iron alloy (Elgiloy alloy), cobalt-chromium alloy, nickel-chromium alloy (Inconel alloy), and iron-chromium alloy. Among these members, the self-inflating nickel-titanium alloy (nitinol) is preferred from the viewpoint of the high fixing power for the stent graft in blood vessels and corrosion resistance. The stent may have any design of a conventional technique. A type that expands with a balloon may be applied to the stent, instead of a self-inflating type. The stent may assume, for example, a monofilament, multifilament, or tape-like structure. Two or more of these structures may be combined. In the case of requiring expanding force or strength, it is preferred to use a monofilament stent. A tape-like stent is preferred from the viewpoint of a reduced film thickness. As for the size of the stent, a narrower stent is more easily inserted to a catheter. However, too narrow a stent loses expanding force and cannot be fixed in a blood vessel. Thus, the stent is preferably selected to secure expanding force and to be as thinnest as possible.

Examples of the shape of the stent include a linear shape, a zigzag shape, and a diamond shape. A deformable zigzag shape is preferred for graft movement.

In order to attach the stent to the tubular seamless fabric, a continuous wire may be attached thereto in a spiral pattern. Alternatively, the tubular seamless fabric may be fitted with two separated ring-shaped stents or may be partially fitted with a ring-shaped stent.

The tubular seamless fabric of the present embodiment can be attached to the inner face or/and outer face of the stent to prepare a stent graft. For suppressing the inhibition of blood flow by the stent and thrombus, the seamless fabric is preferably attached to the inner face, rather than the outer face, of the stent. Examples of the method for attaching the tubular seamless fabric to the stent include suture using a thread, fixation using an adhesive, and fixation using a rivet. Suture using a thread is preferred from the viewpoint of joint strength and close contact.

Examples of the suture thread include, but are not limited to, fibers of polyester, polypropylene, polyamide, polyurethane, polyethylene terephthalate, polybutylene terephthalate, polycyclohexane terephthalate, and fluorine resins such as PTFE and ETFE. These threads may each be made of a monofilament, a multifilament, or a superfine fiber. Use of the superfine fiber can be decrease the size of suture holes, thus helping to produce a low water permeability. One or two or more fiber materials in combination can be used according to a purpose. The combined fibers may be used as a composite fiber comprising the two or more fibers twisted with each other or may be used as separate fibers in the warp yarn and the weft yarn, respectively, of the woven fabric, or may be used partially in certain sections. Polyester such as polyethylene terephthalate or a fluorine resin such as PTFE or ETFE is preferred from the viewpoint of high in vivo structural stability, prolonged durability, and good handleability. Polyester such as polyethylene terephthalate or a fluorine resin such as PTFE or ETFE having a glass transition temperature of 50° C. or higher that prevents fiber strength from being reduced due to change in temperature in vivo is more preferred.

Examples of the adhesive include, but are not limited to, polyester resins and polypropylene resins. The fixation using the adhesive, as compared with suture, does not damage the seamless fabric. Therefore, there is no chance of endoleak from suture holes. Hence, the fixation using the adhesive is more preferable than suture. A radiopaque marker may be incorporated into the stent graft for the positioning of stent graft deployment, thereby improving X-ray visibility. Examples of the radiopaque marker include gold, tantalum, and noble metals such as platinum and iridium. Gold or platinum also has very high radiopacity and is therefore more preferred from the viewpoint of enhancing visibility.

The stent graft of the present embodiment may be fitted with an anchoring stent. The anchoring stent works to hook the stent in the inner wall of the aorta or the like. The presence of the anchoring stent prevents the stent graft from being shifted by the long-term beating of a blood vessel.

A hole can be made in the tubular seamless fabric of the present embodiment so as not to clog blood vessels near the stent graft placement site. The periphery of the hole is preferably treated by sewing, heat melting, or the like to prevent tear. The number or diameter of the hole is preferably identical to the number or diameter of blood vessels near the stent graft placement site. Examples of the shape of the hole include, but are not limited to, round, oval, triangle, square, polygonal, and random shapes. For confirming the position of the hole during operation, it is more preferred to attach an opaque marker to the periphery of the hole.

In a preferred embodiment, the stent graft is inserted into a catheter and delivered into a blood vessel. The stent graft of the present embodiment is thin and highly flexible, with a fabric thickness of 90 μm or smaller, and can therefore be inserted into a low profile catheter, and consequently can be easily delivered into blood vessels with low risk of damage to vascular walls. The catheter can employ various known techniques, such as a tube type or a balloon type for stent delivery. Also, the stent graft inserted in a low profile catheter according to the present invention can be delivered into and indwelled in a blood vessel by use of delivery systems of various known techniques. Use of the tubular seamless fabric of the present embodiment as a stent graft fabric allows a stent graft to have a low profile, which can reduce the physical and economical burdens on patients in such a way as to shorten the inpatient periods, and can also reduce risks such as vascular wall damage. Furthermore, the provision of the tubular seamless fabric can widen the range of applications even to cases that have hitherto been excluded as targets of transcatheter intravascular treatment, such as females and Asians that have narrower arteries.

Hereinafter, the methods for producing the superfine fiber and the seamless fabric of the present embodiment will be described. However, the present invention is not intended to be limited by these methods.

Polyethylene terephthalate (PET) will be taken as an example of the superfine fiber, though the superfine fiber is not limited to this material. For this polyethylene terephthalate (PET) polymer, it is preferred to adopt a direct melt spinning method in which the polymer is melt spun and then drawn to produce a superfine fiber. The melt spinning machine used may be a known spinning machine equipped with a dryer, an extruder, and a spinning head. The molten PET is discharged from a plurality of discharge nozzles in a spinneret mounted on the spinning head, and immediately after spinning, blasted with cooling air from a cooling device provided under the spinneret surface for cooling to solidification, and spun into a multifilament.

For the production of the superfine fiber of polyethylene terephthalate (PET), a PET polymer with a reduced viscosity of 0.85 dl/g or greater is preferably used from the viewpoint of exhibiting fiber strength and achieving high toughness. The upper limit of the reduced viscosity of the starting PET polymer is 1.60 dl/g from the viewpoint of spinning stability. The spinneret surface temperature during spinning is preferably controlled within the range of 290° C. or higher and 320° C. or lower. When the discharge nozzle is a multiple array, the spinneret surface temperature distribution (the temperature distribution from the outermost array to the innermost array) is preferably within 10° C. The reduced viscosity and the spinning temperature are changed according to the type and physical properties of the fiber.

In the present embodiment, the number of discharge nozzles per spinneret is preferably 20 to 1500 bored holes. The arrangement of the discharge nozzles is not particularly limited and is a circumferential arrangement, crossing arrangement, or the like. The circumferential arrangement preferably has multiple circumferential rows for the purpose of increasing the number of nozzles. The number of rows in the multiple circumferential arrangement, the distance between rows, the distance between the discharge nozzles on circumferential rows, and the design of the cooling air flow passage can be arbitrarily determined within the ranges of the desired number of monofilaments, single filament fineness, and allowable spinneret size.

The hole diameter of the discharge nozzle is preferably 0.15 mmϕ or smaller and 0.05 mmϕ or larger.

In the method for producing the superfine fiber, the discharged yarn is preferably bundled at a location of 5 cm or more and 50 cm or less from the direct bottom of the spinneret, from the viewpoint of minimizing swinging of the yarn and improving spinning stability. After the bundling, preferably, a finishing agent is added to the fiber bundle, and spinning is carried out at 300 m/min or more and 3000 m/min or less from the viewpoint of spinning efficiency and high toughness. The oil application rate of the finishing agent is preferably 1 wt % or more and 3 wt % or less from the viewpoint of bulk finishing and suitability for textile processing.

In the method for producing the superfine fiber, tangling treatment at the undrawn yarn stage or drawn yarn stage is preferred from the viewpoint of reducing fluff and yarn breakage during bulking treatment and textile processing. The tangling treatment preferably adopts a known tangling nozzle with the number of tangles being in the range of 1 to 50/m.

Twisted yarn is produced using the superfine fiber obtained by the production method described above. The production of the twisted yarn can employ a known or common yarn twister. Examples thereof include known yarn twisters such as a ring twister, a double twister, an Italian twister, and a covering machine. The form of the twisted yarn may be single twist yarn in which one or two or more filaments are paralleled and twisted in the S or Z direction, or may be piled yarn in which two such single twist yarns are paralleled and further second twisted.

A tubular seamless fabric can be produced using the twisted yarn of the superfine fiber obtained by the production method described above. The loom used to produce the tubular seamless fabric is not particularly limited. A shuttle loom in which the weft yarn is passed through by the reciprocal movement of a shuttle is preferably used from the viewpoint of minimizing reduction in woven density at the tab sections of the woven fabric (the folded sections of the tubular woven fabric), and attaining a uniform woven fabric thickness. When a fiber with relatively large single filament fineness and total fineness is used to prepare a sack-like woven fabric with a large thickness and a large woven width, for example, an air bag, it is possible to use a shuttleless weaving machine such as an air jet loom, a water jet room, or a rapier loom. However, when the uniform woven fabric having a small thickness and a high density according to the present embodiment is prepared by weaving with such a shuttleless weaving machine, the strength is notably decreased at the tab sections of the woven fabric, causing partial increase in water permeability, and therefore endoleak and the like become crucial defects in use as a stent graft fabric.

The preparation of the tubular seamless fabric requires controlling the raising and lowering of the warp yarn. An apparatus such as a Jacquard opening apparatus or a dobby opening apparatus can be used for this purpose.

For the filling pick count, it is preferred to adjust the speed of a wind-up roll such that the cover factor of the weft yarn is 800 or more. When the cover factor of the weft yarn is 800 or more, both of the weft density and the degree of weft yarn overlap can be improved.

For the adjustment of the number of warps for sleying, the warp yarn can be prepared with a warp yarn cover factor of 800 or more and subjected to sleying. The loom rotation speed is preferably 80 rpm or higher from the viewpoint of productivity. After weaving, it is preferred to carry out scouring treatment aimed at removing the lubricant or the like, and heat setting aimed at stabilizing the form. The tubular seamless fabric thus prepared can be combined with a stent using a suture thread and inserted into a catheter for use as a stent graft.

The fiber used in the present embodiment is preferably a polyester fiber. Particularly, the superfine polyester fiber preferably has tensile strength of 3.5 cN/dtex or more and tensile elongation of 12% or more. The superfine polyester fiber having tensile strength of 3.5 cN/dtex or more can exert excellent dynamic physical properties as a stent graft fabric. On the other hand, it is possible to enhance the tensile strength of the polyester fiber by increasing the draw ratio. However, even if the tensile strength is enhanced to 3.5 cN/dtex or more by drawing, for example, a polyester fiber having tensile elongation less than 12% has poor toughness, leading to tear or breakage due to impact. The tensile strength of the superfine polyester fiber of the present embodiment is more preferably 3.8 cN/dtex or more, further preferably 4.0 cN/dtex or more, from the viewpoint of the stability of the woven fabric in the weaving steps. From the same viewpoint, the tensile elongation of the superfine polyester fiber of the present embodiment is more preferably 15% or more, further preferably 20% or more.

The superfine polyester fiber may be used in at least a portion of the warp yarn and/or the weft yarn of the medical fabric of the present embodiment. Also, the superfine polyester fiber may be used in the whole weft yarn, may be partially used in the weft yarn of the woven fabric, or may be used every few wefts. The same holds true for the warp yarn. The superfine polyester fiber may be used in a portion or the whole of the warp yarn or the weft yarn, and the use ratio can be determined according to a use purpose. Although the superfine polyester fiber tends to generate fluff because of its small single filament fineness, the yarn may be coated with a sizing agent or a lubricant, or handling during weaving may be improved by improving the bundling property of the yarn by way of twisted yarn or the like.

The superfine polyester fiber preferably has a PET component content of 98 wt % or more, i.e., a content of less than 2 wt % of components other than PET. In this context, the components other than PET refer to components incorporated into the molecular chain by copolymerization or the like, copolymerized PET, polyamide, polystyrene, and copolymers thereof that have adhered onto the polyester fiber surface, sea component polymers used for the production of sea-island superfine PET fibers, such as polyethylene and polyvinyl alcohol, and decomposition products of these sea component polymers. In the present embodiment, it is preferred that the components other than PET should not include PET-derived monomers and oligomers such as ethylene glycol, terephthalic acid (TPA), monohydroxyethylene terephthalate (MHET), and bis-2-hydroxyethyl terephthalate (BHET). If the content of the components other than PET is 2 wt % or more, the components elute out into the body when embedded, potentially causing heat release or heterogenization reactions. The content of the components other than PET in the superfine polyester fiber is preferably less than 1 wt %, more preferably less than 0.5 wt %, further preferably zero.

In the medical fabric of the present embodiment, the polyester fiber, particularly, the superfine polyester fiber, can also function effectively as a constituent fiber of a material for implantation into the human body, including artificial blood vessels, artificial fiber fabrics, antiadhesive agents, artificial valves, and the like, in addition to the stent graft fabric. The (superfine) polyester fiber may also function effectively as a constituent fiber of an in vitro material for medical use such as a hemofiltration material, a cell separating membrane, a cell adsorption material, or a cell culturing substrate, in addition to the material for implantation into the human body. Naturally, the polyester fiber, particularly, the superfine polyester fiber, can also be utilized for materials other than those in the medical field, such as clothing materials or materials for filtering or wiping.

In the method for producing the superfine polyester fiber suitable for use in the medical fabric of the present embodiment, a finishing agent can be added to a fiber bundle to improve suitability for subsequent warping and weaving steps. For example, a mineral oil-derived lubricant or a water-soluble lubricant is used as the finishing agent. The oil application rate of the finishing agent is preferably 1 wt % or more and 3 wt % or less, more preferably 1.2 wt % or more and 2.8 wt % or less, further preferably 1.5 wt % or more and 2.5 wt % or less, from the viewpoint of bulk finishing and suitability for textile processing.

In the method for producing the superfine polyester fiber used in the present embodiment, tangling treatment at the undrawn yarn stage or drawn yarn stage is preferred from the viewpoint of reducing fluff and yarn breakage during warping and knitting or weaving, and improving an unwinding property. The tangling treatment preferably adopts a known tangling nozzle with the number of tangles being in the range of 1 to 50/m. The thermal shrinkage stress of the superfine polyester fiber for use in weaving is preferably 0.2 cN/dtex or more in the temperature range of 80° C. or higher and 200° C. or lower, from the viewpoint that the superfine polyester fiber used in the present embodiment secures a thermal shrinkage stress of 0.05 cN/dtex or more as a superfine polyester fiber constituting the woven fabric of a final stent graft product (after sterilization treatment).

Hereinafter, the production of the medical fabric of the present embodiment will be described. In the step of preparing the warp yarn constituting the medical fabric of the present embodiment, a necessary number of warps is wound up on a warp beam using a warping machine, and this warp beam may be loaded in a loom. Alternatively, the warp yarn may be placed onto a loom directly from packages loaded in a creel.

The loom used to produce the seamless tubular fabric of the present embodiment is not particularly limited. Use of a shuttle loom in which the weft yarn is passed through by the reciprocal movement of a shuttle is suitable for the seamless woven fabric and is also preferred for minimizing variation in woven density at the tab sections of the woven fabric (the folded sections of the tubular fabric), and attaining a uniform woven fabric thickness. In the case of using the shuttle loom, three shuttles are used in weaving when the woven fabric has a branched portion having two branches. These three shuttles can be used for the large diameter portion, one of the branches, and the other branch, respectively. Alternatively, in the case of using two shuttles, weaving can be performed using one of the shuttles for the large diameter portion and one of the branches and the other shuttle for the other branch. The unwinding of the weft yarn from the shuttle at uniform tension is effective for producing a high quality tubular woven fabric having no wrinkles by weaving. A structure using a plurality of springs or the like is preferred.

In the preparation of the tubular woven fabric according to the present embodiment by weaving, a full width temple may be used for the purpose of stabilizing cloth fell, attaining the uniform thickness and diameter of the woven fabric, and minimizing yarn breakage or the like during processing. It is preferred to select a material with a low frictional coefficient for the full width temple member at the section contacting with the woven fabric, and to use a tacky and antiskid material with smooth surface for wind-up roll surface. An appropriate design may be selected for the structure of the full width temple and the frictional coefficient of the member used, according to the single filament fineness or total fineness of the yarn used and the woven density of the warp yarn or the weft yarn.

The preparation of the tubular seamless fabric by weaving requires controlling the raising and lowering of the warp yarn. An apparatus such as a Jacquard opening apparatus or a dobby opening apparatus can be used for this purpose. An electronic Jacquard machine is particularly preferably used for easily producing the woven texture of the branched portion.

After weaving, scouring treatment aimed at removing the lubricant or the like, and heat setting aimed at stabilizing the form is carried out. The scouring temperature and time, the heat setting temperature and time, and tension in these steps are not particularly limited.

In the case of heat setting the medical fabric of the present embodiment, it is preferred to produce metal tools for heat setting by using a stainless tube having the diameter of the large diameter portion and a tapered stainless tube having the diameter of the branched portion, and reducing a portion corresponding to decrease in the diameter caused by the single texture near the branched portion. In this case, from the viewpoint of workability, the metal tools are separately produced for the large diameter and for the branches and preferably have structures by which the metal tools can be inserted to the woven fabric to be heat set from above and below, and fixed in the woven fabric to fix the woven fabric having the desired diameter without wrinkles.

EXAMPLES

Hereinafter, the present invention will be specifically described with reference to Examples. However, the present invention is not limited by these Examples. The main measurement values of physical properties were obtained by the following measurement methods.

(1) Reduced Viscosity ($\eta sp/c$)

The reduced viscosity ($\eta sp/c$) is measured as follows.

For polyethylene terephthalate (PET), 0.35 g of a polyethylene terephthalate (PET) sample is dissolved in 0.25 deciliters of 1,1,1,3,3,3-hexafluoro-2-propanol (HFIP) at room temperature to prepare a dilute solution. The solvent and the amount of the solvent can be changed according to the type of the polymer.

A Ubbelohde viscosity tube (tube diameter: 0.03) is used to measure the number of seconds of dropping of the dilute solution and the HFIP solvent at 25° C., and the relative viscosity (lisp) is determined.

The relative viscosity (lisp) is divided by the polymer concentration C (g/dl) to calculate the reduced viscosity $\eta sp/c$.

(2) Total Fineness and Single Filament Fineness

The total fineness (dtex) is a value obtained by winding the fiber bundle 50 times around a skein with a 1 m circumference, measuring the weight of the yarn, and multiplying the value by 200. The single filament fineness (dtex) is a value obtained by dividing the total fineness thus determined by the number of monofilaments.

(3) Crimp Percentage

The crimp percentage was measured by the method described in JIS L-1096 (2010) 8.7 Method B.

A 200 mm distance was marked at 3 locations each in the warp direction and the weft direction. The warp yarn and the weft yarn within this mark were each raveled. The length (mm) of the yarn tightened under initial load was measured, and the crimp percentage was calculated.

(4) Total Fineness and Single Filament Fineness of Removed Yarns (Evaluation Using Woven Fabric)

The measurement based on JIS L-1096 (2010) 8.9.1.1 Method A was conducted.

Three 200 mm×200 mm test specimens were sampled. 25 warps and 25 wefts per specimen were raveled. The mass (mg) was measured, and the fineness was calculated. The single filament fineness is a value obtained by dividing the total fineness thus determined by the number of monofilaments.

(5) Twist Number of Removed Yarns (Evaluation Using Woven Fabric)

The measurement based on JIS L-1096 (2010) Annex I was conducted. A removed yarn from textile was measured at a gripping interval of 20 cm using a twist counter, and the measurement value was converted to a twist number per m.

(6) Twist Coefficient A of Removed Yarns

The twist coefficient A of removed yarns was calculated from the total fineness of removed yarns in (4) and the twist number of removed yarns in (5) according to the following expression:

Twist coefficient $A$ of removed yarns=(Twist number of removed yarns)×(Total fineness of removed yarns)$^{1/2}$ (7) Warp Yarn Tension A yarn tension measurement apparatus was used to measure tension applied per warp at the central parts of a warp beam and a back roller during operation of a loom. Five largest values and five smallest values for the loop operating time of 10 minutes were extracted and averaged. A value obtained by dividing the obtained tension per warp by the fineness was used.

(8) Woven Densities of Warp Yarn and Weft Yarn

The measurement based on JIS L-1096 (2010) 8.6.1 was conducted. A sample was placed on a flat stage, and the numbers of warps and wefts in a 2.54 cm zone were counted at 5 different locations excluding unnatural wrinkles and tension, and their respective averages were calculated.

(9) Cover factors of warp yarn or weft yarn

The cover factors were calculated from the woven densities of (7) according to the following expressions:

Warp yarn cover factor=(Warp yarn total fineness: dtex)$^{1/2}$×(Warp yarn woven density: the number of warps/2.54 cm)

Weft yarn cover factor=(Weft yarn total fineness: dtex)$^{1/2}$×(Weft yarn woven density: the number of wefts/2.54 cm)

The warp yarn or weft yarn total fineness used was the total fineness of removed yarns evaluated using a woven fabric in (4).

(10) Degree of Warp Yarn Overlap (TT) and Degree of Weft Yarn Overlap (WW)

Figure 2:
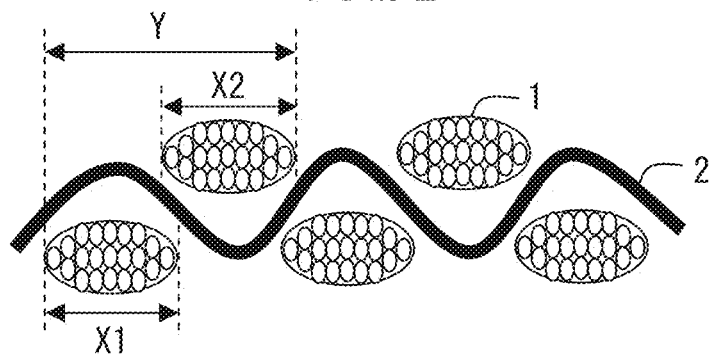
FIG. 2 is a cross-sectional schematic view showing one example of the medical fabric of the present embodiment and illustrating a degree of weft yarn overlap (WW)

FIG. 2 shows the cross sectional state in the warp direction of a woven fabric. A sample was loaded on a SEM sample stage by an ordinary method. In order to cut out the yarn cross section vertically and orderly, the woven fabric was cut with a blade along the warp yarn and between warps using a ruler. As a result, the state of the weft yarn cross section orthogonal to the arbitrary warp yarn shape can be observed. Likewise, the measurement of the degree of warp yarn overlap (TT) requires photographing a warp yarn cross section. Thus, the woven fabric was cut with a blade along the weft yarn and between wefts. Then, the cross section was photographed by SEM with a magnification that allowed approximately 4 to 6 multifilaments to visibly fit inside one field of view (magnification: 200×).

The degree of warp yarn overlap (TT) and the degree of weft yarn overlap (WW) were calculated from X1, X2, and Y values measured from the cross sectional images taken in the warp and weft directions of the woven fabric, according to the following expression:

$$\text{Degree of yarn overlap} = (X1 + X2)/Y$$

wherein X1 represents the width of an arbitrary yarn cross section, X2 represents the width of a yarn cross section adjacent to X1, and Y represents the width from X1 to X2.

For the measurement of the degree of warp yarn overlap (TT), the value is calculated from the image of the warp yarn cross section according to the expression described above. Also, for the measurement of the degree of weft yarn overlap (WW), the value is calculated from the image of the weft yarn cross section according to the expression described above.

Figure 3:
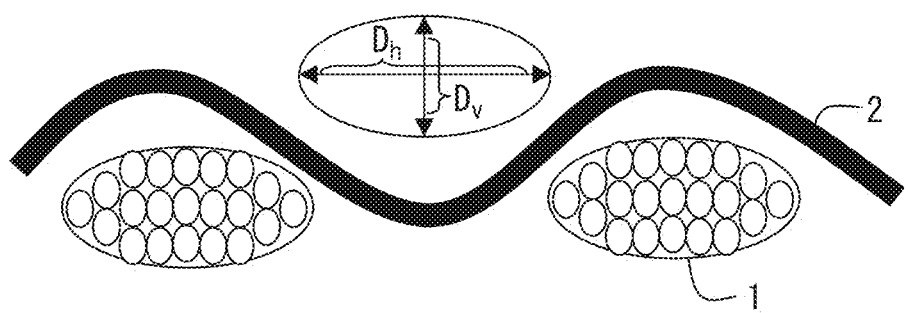
FIG. 3 is a cross-sectional schematic view showing one example of the medical fabric of the present embodiment and illustrating the ratio of a horizontal diameter to a vertical diameter (Dh/Dv) on the weft yarn cross section.

(11) Ratio of Horizontal Diameter to Vertical Diameter on Warp Yarn or Weft Yarn Cross Section Cross sectional images of a woven fabric were taken as described in (10). As shown in FIG. 3, the diameter in the vertical direction (Dv) and the diameter in the horizontal direction (Dh) were measured for an arbitrary warp and weft from the cross sectional images of the woven fabric, and the ratio of the horizontal diameter to the vertical diameter, Dh/Dv, was calculated.

(12) Warp/Weft Yarn Single Filament Fineness Ratio of Single Filament Fineness Dw (Dtex) of Warp Yarn to Single Filament Fineness Df (Dtex) of Weft Yarn The single filament fineness Dw (dtex) of the warp yarn and the single filament fineness Df (dtex) of the weft yarn were measured as described in (2), and Dw/Df was calculated.

(13) Intra-Yarn Single Filament Fineness Ratio S

Yarn cross sections were photographed by SEM with a magnification that allowed the multifilament of the weft yarn or the warp yarn to visibly fit inside the field of view (magnification: 200×). The observed cross sectional shape was printed, and the intra-yarn single filament fitness ratio S was calculated by determining the ratio between the largest weight and the smallest weight by the cutout weight method. When the yarn was made of plural types of filaments, the density of a substance constituting each monofilament was taken into consideration.

Intra-yarn single filament fineness ratio S=Largest single filament weight/Smallest single filament weight

(14) Warp Yarn Crimp Angle

Cross sectional images of a woven fabric were taken as described in (10). As shown in FIG. 4, a horizontal line was drawn between arbitrary adjacent wefts in the cross sectional image of the woven fabric, and the angle θ of a portion intersecting the inclined line of the warp yarn was measured.

(15) Thickness of Woven Fabric

The thickness of a fabric was measured using a thickness gauge with a 1 N load at n=5 after 10 seconds for settling, and the average was calculated.

(16) Tear Force

The tear force of a fabric was measured according to JIS L-1096 6.15.1 (single tongue method). This measurement was conducted both warpwise and weftwise, and the smaller value was used as the tear force of the fabric.

(17) Water Permeability Before and after Needle Puncture of Woven Fabric

The water permeability of a sample prepared with a shuttle loom of a Jacquard opening apparatus was measured by the following method: the water permeability of the woven fabric is measured before and after needle puncture, according to ANSI/AAMI/ISO 7198:1998/2001. In this test, the water permeability after needle puncture is a value measured after arbitrary passing of a tapered 3/8 needle 10 times through the fabric in a 1 cm² area. The measurement was conducted at n=5 both before and after needle puncture, and the averages of the water permeabilities W (cc/cm²/min) before and after needle puncture were calculated.

(18) Water Permeability of Tubular Fabric of Branched Portion (Water Permeability (l/Min) Including Boundary Portion)

Water permeability measurement is conducted with reference to ANSI/AAMI/ISO 7198:1998/2001. A tubular medical fabric having a branched portion is prepared such that the total length is 100 mm, the length of a large diameter portion is 50 mm, and the length of the branched portion is 50 mm. The large diameter portion of this woven fabric is allowed to cover a metal tube circumferentially coated with rubber, firmly fixed in circumference with a metal band, and fastened so as not to cause leak. In this operation, the length from the end of the metal band to the boundary portion (boundary between the large diameter portion and the branched portion) is set to 30 mm. However, the metal tube has a hollow structure sufficient for water passage.

Likewise, the end of the branched portion is also allowed to cover a metal tube circumferentially coated with rubber, firmly fixed in circumference with a metal band, and fastened so as not to cause leak. The length from the end of the metal band to the boundary portion is set to 30 mm. The measurement is conducted at n=5, and the average is calculated.

(19) Tensile Strength and Tensile Elongation

The tensile strength and the tensile elongation were measured according to JIS-L-1013.

(20) Burst Strength of Woven Fabric

The burst strength test of a woven fabric was carried out at n=5 according to ANSI/AAMI/ISO 7198:1998/2001, and the smallest value among the measurement values of n5 is shown.

(21) Crimp Percentage

The test was conducted on warp yarn and weft yarn extracted from a woven fabric according to JIS L-1096 8.7 Method b. 20 warps and 20 wefts were used in the measurement, and the averages are shown.

(22) Porosity

A woven fabric is embedded with a resin such as Technovit (Kulzer Co. Germany), and a 3 μm-thick strip is prepared using a glass knife and photographed with an optical microscope at 400× magnification. The porosity is calculated according to the following expression, from area measurement at the fiber sections and fiber gap sections on the photograph.

Porosity (%)=(Total area of the measured fabric−
Area occupied by individual superfine fibers)/
(Total area of the measured fabric)×100

The image area measurement is accomplished using common image processing computer software, for example, NIH Image.

(23) Catheter Insertability

A woven fabric sutured with a stent was properly folded and evaluated for whether or not to be inserted in a cylindrical catheter with an inner diameter of 6 mm. A sample that was able to be effortlessly inserted was evaluated as good (indicated by "A"); a sample that had difficulty with insertion was evaluated as fair (indicated by "B"); and a sample that was unable to be inserted was evaluated as poor (indicated by "C"). The evaluation was conducted at n=5.

Example 1

<Superfine (Ultrafine) Fiber>

Polyethylene terephthalate (PET) was used as a starting material, and melt spinning was performed to wind up 65 dtex undrawn yarn.

The properties of the starting PET polymerized with germanium catalyst were as follows.

Reduced viscosity (ηsp/c): 1.162 dl/g
Titanium content: 2 ppm
Diethylene glycol content: 0.8 wt %
Oligomer content: 1.2 wt %

The spinneret used was a 5-row spinneret bored at a hole diameter of 0.08 mmϕ, with a distance of 1.7 mm between discharge nozzles on the innermost row and a distance of 8 mm between all the rows. Cooling of the yarn was accomplished basically using a cooling air blasting apparatus with an air diffuser at an elevation angle of 37°. Spinning was otherwise carried out under the conditions (spinneret surface temperature: 303° C., spinneret surface temperature distribution: 3° C., hot zone length: 36 mm, cooling air temperature: 13° C., cooling air speed: 1 m/s, speed variation: 0.07, bundling location: 26.5 cm), and undrawn yarn was taken up at 2000 m/min [hot zone: zone controlled to an atmosphere temperature of 150° C. or higher (perpendicular distance from the center section of spinneret surface), cooling air temperature: temperature of cooling air blasted from the cooling air blasting apparatus (using a thermoheater for the temperature adjustment of cooling air), speed variation: value represented as a standard deviation for the variation of speed of cooling air blasted from the cooling air blasting surface, bundling location: location where discharged fiber bundles are bundled]. The undrawn yarn thus taken up was subjected to drawing heat treatment with a drawing machine having a known heated roll, at a first roll temperature of 75° C. and a second roll temperature of 130° C. for fiber physical properties of 4.5 cN/dtex tensile strength and 30% tensile elongation, and tangling treatment (10/m) using predetermined tangling nozzles to obtain a superfine fiber.

In addition to the superfine fiber, a regular fiber was also obtained by drawing heat treatment for fiber physical properties of 4.5 cN/dtex tensile strength and 30% tensile elongation, and tangling treatment (10/m) using known tangling nozzles.

<Warp Yarn and Weft Yarn>

Weft yarn having total fineness of 30.3 dtex/300 filaments was prepared by the spinning described above.

Warp yarn having total fineness of 39.4 dtex/24 filaments was prepared by performing melt spinning using a suitably selected spinneret and further setting a draw ratio.

<Twisted Yarn>

The warp yarn and the weft yarn were twisted at 500 T/m (in the S direction) and 100 T/m (in the S direction), respectively, using a known yarn twister to prepare twisted yarn.

<Weaving>

The warp yarn and the weft yarn thus obtained were used in weaving using a shuttle loom and a Jacquard opening apparatus. The reed width and the number of warps were adjusted to attain a warp yarn cover factor of 800 or more. The system was operated with a warp yarn tension of 0.9 cN/dtex and a loom rotation speed of 80 rpm to prepare a plain weave tubular seamless fabric having an inner diameter of 50 mm. This woven fabric was further finished by scouring and heat setting. Results of evaluating the obtained fabric is shown in Tables 1 and 2 below.

Example 2

<Superfine Fiber>

Polyethylene terephthalate (PET) was used as a starting material, and melt spinning was performed to wind up 140 dtex undrawn yarn. A superfine fiber was prepared under the same conditions as in Example 1.

<Warp Yarn and Weft Yarn>

Weft yarn having total fineness of 72.4 dtex/450 filaments was prepared by the spinning described above.

Warp yarn having total fineness of 34.1 dtex/24 filaments was prepared by performing melt spinning using a suitably selected spinneret and further setting a draw ratio.

<Twisted Yarn>

The warp yarn and the weft yarn were twisted at 500 T/m (in the S direction) and 100 T/m (in the S direction), respectively, using a known yarn twister to prepare twisted yarn.

<Weaving>

A plain weave tubular seamless fabric having an inner diameter of 50 mm was prepared under the same conditions as in Example 1 using the warp yarn and the weft yarn thus obtained. This woven fabric was further finished by scouring and heat setting. Results of evaluating the obtained fabric is shown in Tables 1 and 2 below.

Example 3

<Superfine Fiber>

A superfine fiber was prepared under the same conditions as in Example 1.

<Warp Yarn and Weft Yarn>

Weft yarn having total fineness of 20.1 dtex/155 filaments was prepared by the spinning described above. Warp yarn having total fineness of 34.1 dtex/24 filaments was prepared by spinning under the same conditions as in Example 2.

<Twisted Yarn>

The warp yarn and the weft yarn were twisted at 500 T/m (in the S direction) and 100 T/m (in the S direction), respectively, using a known yarn twister to prepare twisted yarn.

<Weaving>

A plain weave tubular seamless fabric having an inner diameter of 50 mm was prepared under the same conditions as in Example 1 using the warp yarn and the weft yarn thus obtained. This woven fabric was further finished by scouring and heat setting. Results of evaluating the obtained fabric is shown in Tables 1 and 2 below.

Example 4

<Superfine Fiber>

A superfine fiber was prepared under the same conditions as in Example 1.

<Warp Yarn and Weft Yarn>

Weft yarn having total fineness of 10.2 dtex/70 filaments was prepared.

Warp yarn having total fineness of 34.1 dtex/24 filaments was prepared by spinning under the same conditions as in Example 2.

<Twisted Yarn>

The warp yarn and the weft yarn were twisted at 500 T/m (in the S direction) and 100 T/m (in the S direction), respectively, using a known yarn twister to prepare twisted yarn.

<Weaving>

A plain weave tubular seamless fabric having an inner diameter of 50 mm was prepared under the same conditions as in Example 1 using the warp yarn and the weft yarn thus obtained. This woven fabric was further finished by scouring and heat setting. Results of evaluating the obtained fabric is shown in Tables 1 and 2 below.

Example 5

<Superfine Fiber>

A superfine fiber was prepared under the same conditions as in Example 1.

<Warp Yarn and Weft Yarn>

Weft yarn having total fineness of 20.1 dtex/155 filaments was prepared by the spinning described above.

Warp yarn having total fineness of 34.1 dtex/24 filaments was prepared by spinning under the same conditions as in Example 2.

<Twisted Yarn>

The warp yarn and the weft yarn were twisted at 1000 T/m (in the S direction) and 400 T/m (in the S direction), respectively, using a known yarn twister to prepare twisted yarn. The warp yarn having a high twist number was steam set in vacuum at 70° C. for 30 minutes to carry out twist setting.

<Weaving>

A plain weave tubular seamless fabric having an inner diameter of 50 mm was prepared under the same conditions as in Example 1 using the warp yarn and the weft yarn thus obtained. This woven fabric was further finished by scouring and heat setting. Results of evaluating the obtained fabric is shown in Tables 1 and 2 below.

Example 6

<Superfine Fiber>

A superfine fiber was prepared under the same conditions as in Example 1.

<Warp Yarn and Weft Yarn>

Weft yarn having total fineness of 20.1 dtex/155 filaments was prepared by the spinning described above.

Warp yarn having total fineness of 34.1 dtex/24 filaments was prepared by spinning under the same conditions as in Example 2.

<Twisted Yarn>

The warp yarn and the weft yarn were twisted at 200 T/m (in the S direction) and 300 T/m (in the S direction), respectively, using a known yarn twister to prepare twisted yarn.

<Weaving>

A plain weave tubular seamless fabric having an inner diameter of 50 mm was prepared under the same conditions as in Example 1 using the warp yarn and the weft yarn thus obtained. This woven fabric was further finished by scouring and heat setting. Results of evaluating the obtained fabric are shown in Tables 1 and 2 below.

Example 7

<Superfine Fiber>

A superfine fiber was prepared under the same conditions as in Example 1.

<Warp Yarn and Weft Yarn>

Weft yarn having total fineness of 30.3 dtex/300 filaments was prepared by the spinning described above. Warp yarn having total fineness of 30.3 dtex/150 filaments was prepared by performing melt spinning using a suitably selected spinneret and further setting a draw ratio.

<Twisted Yarn>

The warp yarn and the weft yarn were twisted at 500 T/m (in the S direction) and 100 T/m (in the S direction), respectively, using a known yarn twister to prepare twisted yarn.

<Weaving>

A plain weave tubular seamless fabric having an inner diameter of 50 mm was prepared under the same conditions as in Example 1 using the warp yarn and the weft yarn thus obtained. This woven fabric was further finished by scouring and heat setting. Results of evaluating the obtained fabric are shown in Tables 1 and 2 below.

Example 8

<Superfine Fiber>

A superfine fiber was prepared under the same conditions as in Example 1.

<Warp Yarn and Weft Yarn>

Weft yarn having total fineness of 50.2 dtex/126 filaments was prepared by the spinning described above.

Warp yarn having total fineness of 39.4 dtex/24 filaments was prepared under the same conditions as in Example 1.

<Twisted Yarn>

The warp yarn and the weft yarn were twisted at 500 T/m (in the S direction) and 100 T/m (in the S direction), respectively, using a known yarn twister to prepare twisted yarn.

<Weaving>

A plain weave tubular seamless fabric having an inner diameter of 50 mm was prepared under the same conditions as in Example 1 using the warp yarn and the weft yarn thus obtained. This woven fabric was further finished by scouring and heat setting. Results of evaluating the obtained fabric are shown in Tables 1 and 2 below.

Example 9

<Superfine Fiber>

A superfine fiber was prepared under the same conditions as in Example 1.

<Warp Yarn and Weft Yarn>

Weft yarn having total fineness of 30.3 dtex/300 filaments was prepared by the spinning described above.

Warp yarn having total fineness of 39.4 dtex/24 filaments was prepared under the same conditions as in Example 1.
<Twisted Yarn>
The warp yarn and the weft yarn were twisted at 900 T/m (in the S direction) and 100 T/m (in the S direction), respectively, using a known yarn twister to prepare twisted yarn.
<Weaving>
The warp yarn and the weft yarn thus obtained were used in weaving using a shuttle loom and a Jacquard opening apparatus. The reed width and the number of warps were adjusted to attain a warp yarn cover factor of 800 or more. The system was operated with a warp yarn tension of 0.1 cN/dtex and a loom rotation speed of 80 rpm to prepare a plain weave tubular seamless fabric having an inner diameter of 50 mm. This woven fabric was further finished by scouring and heat setting. Results of evaluating the obtained fabric is shown in Tables 1 and 2 below.

Example 10

<Superfine Fiber>
A superfine fiber was prepared under the same conditions as in Example 1.
<Warp Yarn and Weft Yarn>
Weft yarn having total fineness of 20.1 dtex/155 filaments was prepared by the spinning described above.
Warp yarn having total fineness of 34.1 dtex/24 filaments was prepared by spinning under the same conditions as in Example 2.
<Twisted yarn>
The warp yarn and the weft yarn were twisted at 700 T/m (in the S direction) and 50 T/m (in the S direction), respectively, using a known yarn twister to prepare twisted yarn.
<Weaving>
A plain weave tubular seamless fabric having an inner diameter of 50 mm was prepared under the same conditions as in Example 9 using the warp yarn and the weft yarn thus obtained. This woven fabric was further finished by scouring and heat setting. Results of evaluating the obtained fabric is shown in Tables 1 and 2 below.

Example 11

<Superfine Fiber>
A superfine fiber was prepared under the same conditions as in Example 1.
<Warp Yarn and Weft Yarn>
Weft yarn having total fineness of 20.1 dtex/155 filaments was prepared by the spinning described above.
Warp yarn having total fineness of 34.1 dtex/24 filaments was prepared by spinning under the same conditions as in Example 2.
<Twisted Yarn>
The warp yarn and the weft yarn were twisted at 500 T/m (in the S direction) and 350 T/m (in the S direction), respectively, using a known yarn twister to prepare twisted yarn.
<Weaving>
A plain weave tubular seamless fabric having an inner diameter of 50 mm was prepared under the same conditions as in Example 1 using the warp yarn and the weft yarn thus obtained. This woven fabric was further finished by scouring and heat setting. Results of evaluating the obtained fabric is shown in Tables 1 and 2 below.

Comparative Example 1

<Warp Yarn and Weft Yarn>
Warp yarn and weft yarn both having total fineness of 39.4 dtex/24 filaments were prepared by spinning under the same conditions as in Example 1.
<Twisted Yarn>
The warp yarn and the weft yarn were twisted at 500 T/m (in the S direction) and 100 T/m (in the S direction), respectively, using a known yarn twister to prepare twisted yarn.
<Weaving>
The warp yarn and the weft yarn thus obtained were used in weaving using a shuttle loom and a Jacquard opening apparatus. The reed width and the number of warps were adjusted to attain a warp yarn cover factor of 800 or more. The system was operated with a warp yarn tension of 0.1 cN/dtex and a loom rotation speed of 80 rpm to prepare a plain weave tubular seamless fabric having an inner diameter of 50 mm. During the weaving, yarn breakage or fluff in the warp yarn or the weft yarn was visually confirmed. This woven fabric was further finished by scouring and heat setting. Results of evaluating the obtained fabric is shown in Tables 1 and 2 below.

Comparative Example 2

<Warp Yarn and Weft Yarn>
Warp yarn having total fineness of 76.1 dtex/30 filaments and weft yarn having total fineness of 39.4 dtex/24 filaments were prepared by performing melt spinning using a suitably selected spinneret and further setting a draw ratio.
<Twisted Yarn>
The warp yarn and the weft yarn were twisted at 500 T/m (in the S direction) and 100 T/m (in the S direction), respectively, using a known yarn twister to prepare twisted yarn.
<Weaving>
A plain weave tubular seamless fabric having an inner diameter of 50 mm was prepared under the same conditions as in Comparative Example 1 using the warp yarn and the weft yarn thus obtained. During the weaving, yarn breakage or fluff in the warp yarn or the weft yarn was visually confirmed. This woven fabric was further finished by scouring and heat setting. Results of evaluating the obtained fabric is shown in Tables 1 and 2 below.

Comparative Example 3

<Superfine Fiber>
A superfine fiber was prepared under the same conditions as in Example 1.
<Warp Yarn and Weft Yarn>
Weft yarn having total fineness of 20.1 dtex/155 filaments was prepared by the spinning described above.
Warp yarn having total fineness of 34.1 dtex/24 filaments was prepared by spinning under the same conditions as in Example 2.
<Twisted Yarn>
The warp yarn was twisted at 500 T/m (in the S direction) using a known yarn twister, while the weft yarn was used without being twisted.
<Weaving>
A plain weave tubular seamless fabric having an inner diameter of 50 mm was prepared under the same conditions as in Comparative Example 1 using the warp yarn and the weft yarn thus obtained. During the weaving, yarn breakage or fluff in the warp yarn or the weft yarn was visually confirmed. This woven fabric was further finished by scouring and heat setting. Results of evaluating the obtained fabric is shown in Tables 1 and 2 below.

Comparative Example 4

<Superfine Fiber>
A superfine fiber was prepared under the same conditions as in Example 1.
<Warp Yarn and Weft Yarn>
Weft yarn having total fineness of 10.2 dtex/60 filaments was prepared.
Warp yarn having total fineness of 34.1 dtex/24 filaments was prepared by spinning under the same conditions as in Example 2.
<Twisted Yarn>
The warp yarn was twisted at 500 T/m (in the S direction) using a known yarn twister, while the weft yarn was used without being twisted.
<Weaving>
A plain weave tubular seamless fabric having an inner diameter of 50 mm was prepared under the same conditions as in Comparative Example 1 using the warp yarn and the weft yarn thus obtained. During the weaving, yarn breakage or fluff in the warp yarn or the weft yarn was visually confirmed. This woven fabric was further finished by scouring and heat setting. Results of evaluating the obtained fabric is shown in Tables 1 and 2 below.

Comparative Example 5

<Superfine Fiber>
A superfine fiber was prepared under the same conditions as in Example 1.
<Warp Yarn and Weft Yarn>
Weft yarn having total fineness of 30.3 dtex/300 filaments was prepared by the spinning described above.
Warp yarn having total fineness of 39.4 dtex/24 filaments was prepared by spinning under the same conditions as in Example 1.
<Twisted Yarn>
The warp yarn and the weft yarn were twisted at 1000 T/m (in the S direction) and 500 T/m (in the S direction), respectively, using a known yarn twister to prepare twisted yarn.
<Weaving>
A plain weave tubular seamless fabric having an inner diameter of 50 mm was prepared under the same conditions as in Comparative Example 1 using the warp yarn and the weft yarn thus obtained. During the weaving, yarn breakage or fluff in the warp yarn or the weft yarn was visually confirmed. This woven fabric was further finished by scouring and heat setting. Results of evaluating the obtained fabric is shown in Tables 1 and 2 below.

Comparative Example 6

<Superfine Fiber>
A superfine fiber was prepared under the same conditions as in Example 1.
<Warp Yarn and Weft Yarn>
Weft yarn having total fineness of 30.3 dtex/300 filaments was prepared by the spinning described above.
Warp yarn having total fineness of 39.4 dtex/24 filaments was prepared by spinning under the same conditions as in Example 1.
<Twisted Yarn>
The warp yarn and the weft yarn were twisted at 500 T/m (in the S direction) and 500 T/m (in the S direction), respectively, using a known yarn twister to prepare twisted yarn.
<Weaving>
A plain weave tubular seamless fabric having an inner diameter of 50 mm was prepared under the same conditions as in Comparative Example 1 using the warp yarn and the weft yarn thus obtained. During the weaving, yarn breakage or fluff in the warp yarn or the weft yarn was visually confirmed. This woven fabric was further finished by scouring and heat setting. Results of evaluating the obtained fabric is shown in Tables 1 and 2 below.

Comparative Example 7

<Superfine Fiber>
A superfine fiber was prepared under the same conditions as in Example 1.
<Warp Yarn and Weft Yarn>
Weft yarn having total fineness of 30.3 dtex/300 filaments was prepared by the spinning described above.
Warp yarn having total fineness of 39.4 dtex/24 filaments was prepared by spinning under the same conditions as in Example 1.
<Twisted Yarn>
The warp yarn and the weft yarn were both twisted at 2000 T/m (in the S direction) using a known yarn twister to prepare twisted yarn.
<Weaving>
A plain weave tubular seamless fabric having an inner diameter of 50 mm was prepared under the same conditions as in Comparative Example 1 using the warp yarn and the weft yarn thus obtained. During the weaving, yarn breakage or fluff in the warp yarn or the weft yarn was visually confirmed. This woven fabric was further finished by scouring and heat setting. Results of evaluating the obtained fabric is shown in Tables 1 and 2 below.

Comparative Example 8

<Superfine Fiber>
A superfine fiber was prepared under the same conditions as in Example 1.
<Warp Yarn and Weft Yarn>
Weft yarn having total fineness of 30.3 dtex/300 filaments was prepared by the spinning described above.
Warp yarn having total fineness of 39.4 dtex/24 filaments was prepared by spinning under the same conditions as in Example 1.
<Twisted Yarn>
The warp yarn and the weft yarn were twisted at 500 T/m (in the S direction) and 100 T/m (in the S direction), respectively, using a known yarn twister to prepare twisted yarn.
<Weaving>
The warp yarn and the weft yarn thus obtained were used in weaving using a shuttle loom and a Jacquard opening apparatus. The reed width and the number of warps were adjusted to attain a warp yarn cover factor of 800 or more. The system was operated with a warp yarn tension of 3.0 cN/dtex and a loom rotation speed of 80 rpm to prepare a plain weave tubular seamless fabric having an inner diameter of 50 mm. During the weaving, yarn breakage or fluff in the warp yarn or the weft yarn was visually confirmed. As a result, in Comparative Example 8, yarn breakage occurred frequently in the weaving process, which thus failed to produce a fabric. This is probably because due to the warp yarn tension of 1.5 cN/dtex or more, the warp yarn was unable to endure the tensile load, leading to the considerable yarn breakage.

Comparative Example 9

<Superfine Fiber>

A superfine fiber was prepared under the same conditions as in Example 1.

<Warp Yarn and Weft Yarn>

Weft yarn having total fineness of 30.3 dtex/300 filaments was prepared by the spinning described above.

Warp yarn was prepared by performing spinning under the same conditions as in Example 1, and doubling and twisting a multifilament having total fineness of 19.7 dtex/12 filaments and a monofilament having total fineness of 19.7 dtex under conditions of 50 T/m (in the S direction) using a known doubling and twisting machine.

<Twisted Yarn>

The warp yarn and the weft yarn were twisted at 500 T/m (in the S direction) and 100 T/m (in the S direction), respectively, using a known yarn twister to prepare twisted yarn.

<Weaving>

A plain weave tubular seamless fabric having an inner diameter of 50 mm was prepared under the same conditions as in Comparative Example 1 using the warp yarn and the weft yarn thus obtained. During the weaving, yarn breakage or fluff in the warp yarn or the weft yarn was visually confirmed. This woven fabric was further finished by scouring and heat setting. Results of evaluating the obtained fabric is shown in Tables 1 and 2 below.

Examples 1 to 11 had neither yarn breakage nor fluff and satisfactory suitability for the textile processing steps, and the obtained fabrics were able to satisfy the target physical properties (thickness of 90 μm or smaller, and water permeability before and after needle puncture of 300 cc/cm$^2$/min or less). Also, the thickness variation Z was within ±15% for all of the fabrics.

Comparative Examples 1 to 9 were unable to satisfy the water permeability before and after needle puncture.

In Comparative Examples 1 and 2, the warp yarn and the weft yarn were both thick in single filament fineness. The weaving was performed with warp yarn tension less than 0.5 cN/dtex, resulting in a warp yarn crimp angle of 20 degrees or larger, a weft yarn cover factor less than 800, and degrees of weft and warp yarn overlap less than 0.9. Therefore, gaps between adjacent wefts and/or between adjacent warps were large in size, probably resulting in the increased water permeability. In Comparative Example 2, the warp yarn was particularly thick in total fineness. Therefore, the fabric thickness was 90 μm or larger.

In Comparative Examples 3 and 4, the weaving was performed with warp yarn tension less than 0.5 cN/dtex, resulting in a weft yarn cover factor less than 800 and degrees of weft and warp yarn overlap less than 0.9. Therefore, gaps between adjacent wefts and/or between adjacent warps were large in size, probably resulting in the increased water permeability. In Comparative Example 3, the twist coefficient of the weft yarn was 0. Therefore, the tear force was poorer than that of Example 3 and was 3 N or smaller. In Comparative Example 4 as well, the twist coefficient of the weft yarn was 0. Therefore, the tear force was poorer than that of Example 4 and was 3 N or smaller.

In Comparative Example 5, the twist coefficient of the weft yarn was 2000 or more. Therefore, gaps between adjacent wefts were large in size, probably resulting in the increased water permeability.

In Comparative Example 6, the warp yarn tension was less than 0.5 cN/dtex, and the warp/weft twist coefficient ratio B was 1.5 or less. Therefore, gaps between adjacent wefts were large in size, probably resulting in the increased water permeability.

Comparative Example 7 was unable to satisfy the water permeability before and after needle puncture because the twist number exceeded 1000 T/m for both the weft yarn and the warp yarn. Due to this twist number of 1000 T/m or more, the ratio of a diameter in the horizontal direction (Dh) to a diameter in the vertical direction (Dv), Dh/Dv, on the cross section of the woven fabric was less than 1.5 for both the warp yarn and the weft yarn, and the warp yarn and the weft yarn were not flat, with a degree of yarn overlap less than 0.9. Therefore, gaps between adjacent wefts and/or between adjacent warps were large in size, probably resulting in the increased water permeability.

In Comparative Example 8, yarn breakage occurred frequently in the weaving process, which thus failed to produce a fabric. This is probably because due to the warp yarn tension of 1.5 cN/dtex or more, the warp yarn was unable to endure the tensile load, leading to the considerable yarn breakage.

In Comparative Example 9, monofilaments were mixed in the warp yarn. Therefore, the intra-yarn single filament fineness ratio S of the warp yarn exceeded 2. Thus, many gaps were generated between monofilaments, probably resulting in the increased water permeability.

TABLE 1

| | | Warp yarn | | | Weft yarn | | Twist number (T/m) | | Twist coefficient |
| --- | --- | --- | --- | --- | --- | --- | --- | --- | --- |
| | | Total | Removed yarn Total | | Total | Removed yarn Total | | | |
| | Yarn type | fineness/single filament fineness | fineness/single filament fineness | Yarn type | fineness/single filament fineness | fineness/single filament fineness | Warp yarn | Weft yarn | Warp yarn |
| Example 1 | PET | 39.4/1.64 | 47.4/1.97 | PET | 30.3/0.10 | 33.5/0.11 | 500 | 100 | 3442 |
| Example 2 | PET | 34.1/1.42 | 41.2/1.72 | PET | 72.4/0.16 | 79.7/0.18 | 500 | 100 | 3209 |
| Example 3 | PET | 34.1/1.42 | 41.3/1.72 | PET | 20.1/0.13 | 22.9/0.15 | 500 | 100 | 3213 |
| Example 4 | PET | 34.1/1.42 | 41.5/1.73 | PET | 10.2/0.14 | 11.7/0.16 | 500 | 100 | 3221 |
| Example 5 | PET | 34.1/1.42 | 42.3/1.76 | PET | 20.1/0.13 | 24.2/0.16 | 1000 | 400 | 6504 |
| Example 6 | PET | 34.1/1.42 | 41.1/1.71 | PET | 20.1/0.13 | 22.1/0.14 | 200 | 300 | 1282 |
| Example 7 | PET | 30.3/0.20 | 36.5/0.24 | PET | 30.3/0.10 | 33.6/0.11 | 500 | 100 | 3021 |
| Example 8 | PET | 39.4/1.64 | 47.4/1.97 | PET | 50.2/0.4 | 55.3/0.44 | 500 | 100 | 3442 |
| Example 9 | PET | 39.4/1.64 | 49.1/2.04 | PET | 30.3/0.10 | 33.6/0.11 | 900 | 100 | 6306 |
| Example 10 | PET | 34.1/1.42 | 42.5/1.77 | PET | 20.1/0.13 | 24.5/0.16 | 700 | 50 | 4563 |

TABLE 1-continued

| | | | | | | | | | |
|---|---|---|---|---|---|---|---|---|---|
| Example 11 | PET | 34.1/1.42 | 42.2/1.75 | PET | 20.1/0.13 | 23.5/0.15 | 500 | 350 | 3248 |
| Comparative Example 1 | PET | 39.4/1.64 | 46.8/1.95 | PET | 39.4/1.64 | 43.4/1.81 | 500 | 100 | 3421 |
| Comparative Example 2 | PET | 76.1/2.53 | 90.9/3.02 | PET | 39.4/1.64 | 42.8/1.78 | 500 | 100 | 4767 |
| Comparative Example 3 | PET | 34.1/1.42 | 41.5/1.73 | PET | 20.1/0.13 | 23.1/0.15 | 500 | 0 | 3221 |
| Comparative Example 4 | PET | 34.1/1.42 | 41.8/1.74 | PET | 10.2/0.17 | 12.1/0.16 | 500 | 0 | 3233 |
| Comparative Example 5 | PET | 39.4/1.64 | 47.4/1.97 | PET | 30.3/0.10 | 34.1/0.11 | 1000 | 600 | 6885 |
| Comparative Example 6 | PET | 39.4/1.64 | 47.4/1.97 | PET | 30.3/0.10 | 34.8/0.11 | 500 | 500 | 3442 |
| Comparative Example 7 | PET | 39.4/1.64 | 51.3/2.14 | PET | 30.3/0.10 | 39.9/0.13 | 2000 | 2000 | 14325 |
| Comparative Example 8 | PET | 39.4/1.64 | — | PET | 30.3/0.10 | — | 500 | 100 | — |
| Comparative Example 9 | PET | 19.7/1.64 + 19.7/19.7 | 25.2/2.1 + 24.8/24.8 | PET | 30.3/0.10 | 32.7/0.11 | 500 | 100 | 3536 |

| | Twist coefficient Weft yarn | Warp/weft twist coefficient ratio B | Weft yarn tension (cN/dtex) | Warp yarn tension (cN/dtex) | Warp density (no./2.54 cm) | Weft density (no./2.54 cm) | Warp yarn cover factor CFw | Weft yarn cover factor CFw | Sum of warp yarn and weft yarn cover factors CFw + CFf |
|---|---|---|---|---|---|---|---|---|---|
| Example 1 | 579 | 5.9 | 0.2 | 0.9 | 186 | 160 | 1280 | 926 | 2206 |
| Example 2 | 893 | 3.6 | 0.2 | 0.9 | 189 | 100 | 1212 | 896 | 2108 |
| Example 3 | 479 | 6.7 | 0.2 | 0.9 | 210 | 188 | 1350 | 902 | 2252 |
| Example 4 | 342 | 9.4 | 0.2 | 0.9 | 190 | 275 | 1222 | 940 | 2162 |
| Example 5 | 1968 | 3.3 | 0.2 | 0.9 | 193 | 192 | 1253 | 945 | 2198 |
| Example 6 | 1410 | 0.9 | 0.2 | 0.9 | 196 | 197 | 1255 | 925 | 2180 |
| Example 7 | 580 | 5.2 | 0.2 | 0.9 | 194 | 158 | 1175 | 918 | 2093 |
| Example 8 | 744 | 4.6 | 0.2 | 0.9 | 173 | 124 | 1193 | 923 | 2116 |
| Example 9 | 580 | 10.9 | 0.2 | 0.1 | 169 | 168 | 1183 | 976 | 2159 |
| Example 10 | 247 | 18.4 | 0.2 | 0.1 | 191 | 191 | 1243 | 944 | 2187 |
| Example 11 | 1697 | 1.9 | 0.2 | 0.9 | 190 | 193 | 1236 | 938 | 2174 |
| Comparative Example 1 | 659 | 5.2 | 0.2 | 0.1 | 177 | 105 | 1211 | 693 | 1904 |
| Comparative Example 2 | 654 | 7.3 | 0.2 | 0.1 | 127 | 106 | 1212 | 695 | 1907 |
| Comparative Example 3 | 0 | — | 0.2 | 0.1 | 191 | 108 | 1230 | 520 | 1750 |
| Comparative Example 4 | 0 | — | 0.2 | 0.1 | 191 | 148 | 1235 | 515 | 1750 |
| Comparative Example 5 | 3504 | 2.0 | 0.2 | 0.1 | 177 | 157 | 1222 | 918 | 2140 |
| Comparative Example 6 | 2950 | 1.2 | 0.2 | 0.1 | 182 | 121 | 1250 | 711 | 1961 |
| Comparative Example 7 | 12633 | 1.1 | 0.2 | 0.1 | 167 | 113 | 1196 | 711 | 1907 |
| Comparative Example 8 | — | — | 0.2 | 3.0 | — | — | — | — | — |
| Comparative Example 9 | 572 | 6.2 | 0.2 | 0.9 | 168 | 125 | 1190 | 712 | 1902 |

TABLE 2

| | Degree of yarn overlap | | Ratio of horizontal diameter to vertical diameter Dh/Dv | | Intra-yarn single filament fineness ratio S | | Warp/weft single filament fineness ratio Dw/Df | Warp yarn crimp angle θ (degree) | Thickness (μm) |
|---|---|---|---|---|---|---|---|---|---|
| | Warp yarn | Weft yarn | Warp yarn | Weft yarn | Warp yarn | Weft yarn | | | |
| Example 1 | 0.9 | 1.0 | 2.1 | 7.1 | 1.1 | 1.2 | 16 | 11 | 69 |
| Example 2 | 0.9 | 1.0 | 2.5 | 5.1 | 1.2 | 1.1 | 9 | 13 | 88 |
| Example 3 | 0.9 | 1.1 | 2.7 | 6.6 | 1.2 | 1.1 | 11 | 11 | 60 |
| Example 4 | 0.9 | 1.1 | 2.5 | 7.9 | 1.3 | 1.1 | 11 | 10 | 52 |
| Example 5 | 0.9 | 1.0 | 1.6 | 4.9 | 1.2 | 1.3 | 11 | 13 | 62 |
| Example 6 | 0.9 | 1.1 | 2.8 | 6.4 | 1.2 | 1.2 | 12 | 12 | 61 |
| Example 7 | 1.0 | 1.1 | 4.0 | 5.3 | 1.2 | 1.3 | 2 | 12 | 62 |
| Example 8 | 0.9 | 1.0 | 2.2 | 4.1 | 1.2 | 1.2 | 4 | 12 | 76 |
| Example 9 | 0.9 | 1.0 | 1.8 | 5.3 | 1.3 | 1.2 | 16 | 10 | 71 |
| Example 10 | 0.9 | 1.1 | 2.1 | 8.1 | 1.2 | 1.1 | 11 | 10 | 64 |
| Example 11 | 0.9 | 1.0 | 2.4 | 5.9 | 1.3 | 1.2 | 12 | 12 | 61 |
| Comparative | 0.8 | 0.7 | 2.2 | 2.7 | 1.4 | 1.2 | 1 | 22 | 75 |

TABLE 2-continued

| | | | | | | | | | |
|---|---|---|---|---|---|---|---|---|---|
| Example 1 | | | | | | | | | |
| Comparative Example 2 | 0.8 | 0.7 | 2.4 | 4.0 | 1.2 | 1.3 | 2 | 23 | 98 |
| Comparative Example 3 | 0.8 | 0.7 | 2.5 | 4.2 | 1.2 | 1.1 | 12 | 12 | 60 |
| Comparative Example 4 | 0.8 | 0.7 | 2.7 | 3.8 | 1.3 | 1.1 | 11 | 11 | 52 |
| Comparative Example 5 | 0.7 | 0.8 | 2.2 | 5.2 | 1.3 | 1.3 | 16 | 23 | 68 |
| Comparative Example 6 | 0.8 | 0.8 | 2.7 | 4.7 | 1.4 | 1.2 | 16 | 22 | 71 |
| Comparative Example 7 | 0.7 | 0.7 | 1.2 | 1.3 | 1.5 | 1.3 | 16 | 25 | 73 |
| Comparative Example 8 | — | — | — | — | — | — | — | — | — |
| Comparative Example 9 | 0.7 | 0.8 | 2.4 | 6.9 | 11.9 | 1.3 | 16 | 21 | 68 |

| | Burst strength (N) | Tear force (N) | Water permeability | | Porosity of warp yarn (%) | Porosity of weft yarn (%) | Catheter insertability (6 mm hole) |
|---|---|---|---|---|---|---|---|
| | | | Before needle puncture | After needle puncture | | | |
| Example 1 | 286 | 6.1 | 121 | 153 | 21 | 32 | A |
| Example 2 | 387 | 8.1 | 92 | 124 | 19 | 23 | A/B |
| Example 3 | 210 | 4.2 | 125 | 157 | 26 | 38 | A |
| Example 4 | 141 | 3.5 | 183 | 215 | 32 | 51 | A |
| Example 5 | 220 | 4.6 | 220 | 253 | 46 | 51 | A |
| Example 6 | 205 | 4.2 | 161 | 203 | 27 | 49 | A |
| Example 7 | 269 | 4.7 | 94 | 106 | 20 | 22 | A |
| Example 8 | 385 | 7.0 | 113 | 145 | 23 | 28 | A |
| Example 9 | 289 | 6.3 | 188 | 222 | 40 | 43 | A |
| Example 10 | 222 | 4.5 | 166 | 197 | 38 | 33 | A |
| Example 11 | 215 | 4.4 | 179 | 211 | 25 | 49 | A |
| Comparative Example 1 | 347 | 6.1 | 419 | 589 | 74 | 81 | A |
| Comparative Example 2 | 415 | 9.3 | 401 | 557 | 70 | 75 | C |
| Comparative Example 3 | 212 | 2.8 | 311 | 343 | 42 | 74 | A |
| Comparative Example 4 | 144 | 2.1 | 345 | 377 | 45 | 88 | A |
| Comparative Example 5 | 291 | 5.6 | 412 | 444 | 91 | 62 | A |
| Comparative Example 6 | 296 | 5.7 | 365 | 397 | 59 | 82 | A |
| Comparative Example 7 | 332 | 6.2 | 524 | 556 | 91 | 95 | A |
| Comparative Example 8 | — | — | — | — | — | — | A |
| Comparative Example 9 | 282 | 5.5 | 292 | 531 | 66 | 72 | A |

Examples 12 to 14

A polyester fiber that provided total fineness of 36 dtex, single filament fineness of 1.5 dtex, and a twist number of 500 T/m as to yarn extracted from a woven fabric was used in warp yarn. A superfine polyester fiber that provided total fineness of 26 dtex, single filament fineness of 0.17 dtex, and a twist number of 100 T/m as to yarn extracted from the woven fabric was used in weft yarn. A branched tubular seamless fabric was prepared using three shuttles in a shuttle loom equipped with an electronic Jacquard opening apparatus. A large diameter portion was woven at the number of warps of 670, a reed width of 50.0 mm for the warp yarn, and a reed density of 16.8 blades/cm and 8/blade. Subsequently, a branched portion was woven such that: the warps were divided at the middle of textile into 335 warps each for the left and right branches; a single texture was formed before and after the branching point according to the fabric texture of the boundary portion as shown in FIG. 6; and the number of warps applied to the single texture was 24 (Example 12). Likewise, weaving was performed according to the fabric texture of the branched portion shown in FIG. 7 such that: a single texture was formed only in the large diameter portion; and the number of warps applied to the single texture was 20 (Example 13). Also, weaving was performed according to the fabric texture of FIG. 8 where a single texture was formed only in the branched portion (Example 14). Fractional warp yarn was subjected to sleying at an appropriate number for the weaving (the same holds true for the description below).

Examples 15 to 18

A polyester fiber that provided total fineness of 36 dtex, single filament fineness of 1.5 dtex, and a twist number of 500 T/m as to yarn extracted from a woven fabric was used in warp yarn. A superfine polyester fiber that provided total fineness of 36 dtex, single filament fineness of 1.5 dtex, and a twist number of 100 T/m as to yarn extracted from the woven fabric was used in weft yarn. A branched tubular seamless fabric was prepared in the same way as in Examples 12 to 14 using three shuttles in a shuttle loom equipped with an electronic Jacquard opening apparatus. A large diameter portion was woven at the number of warps of 562, a reed width of 49.2 mm for the warp yarn, and a reed density of 19.1 blades/cm and 6/blade. Subsequently, a branched portion was woven such that: the warps were divided at the middle of textile into 281 warps each for the left and right branches; a single texture was formed before and after the branching point according to the fabric texture of the boundary portion as shown in FIG. 6; and the number of warps applied to the single texture was 24 (Example 16). Likewise, weaving was performed according to the fabric texture of FIG. 5 where a single texture was formed neither in the large diameter portion nor in the branched portion (Example 15). Further, weaving was performed such that: the number of warps applied to the single texture was 4 (Example 17) or 44 (Example 18); and the single texture had the fabric texture of FIG. 6 reduced or enlarged.

Example 19

Weaving was performed in the same way as in Example 1 except that a polyester fiber that provided total fineness of 48 dtex, single filament fineness of 0.46 dtex, and a twist number of 100 T/m as to yarn extracted from a woven fabric was used in weft yarn.

Example 20

A superfine polyester fiber that provided total fineness of 27 dtex, single filament fineness of 0.18 dtex, and a twist number of 500 T/m as to yarn extracted from a woven fabric was used in warp yarn. A superfine polyester fiber that provided total fineness of 30 dtex, single filament fineness of 0.2 dtex, and a twist number of 100 T/m as to yarn extracted from the woven fabric was used in weft yarn. A branched tubular seamless fabric was prepared in the same way as in Example 12 using three shuttles in a shuttle loom equipped with an electronic Jacquard opening apparatus. A large diameter portion was woven at the number of warps of 650, a reed width of 49.7 mm for the warp yarn, and a reed density of 32.8 blades/cm and 4/blade. Subsequently, a branched portion was woven such that: the warps were divided at the middle of textile into 325 warps each for the left and right branches; a single texture was formed before and after the branching point according to the fabric texture of the boundary portion as shown in FIG. 6; and the number of warps applied to the single texture was 24.

These prepared woven fabrics were subjected to scouring and heat setting under treatment conditions described below to prepare branched tubular woven fabrics. The respective shuttles were used to weave the large diameter portion and two branches of the branched portion. Therefore, the shuttle carrying the weft yarn for weaving the large diameter portion was switched at the boundary portion to the shuttles carrying the weft yarn for respectively weaving the branches. Thus, the weft yarn was no longer continuous at the boundary portion.

Figure 9:
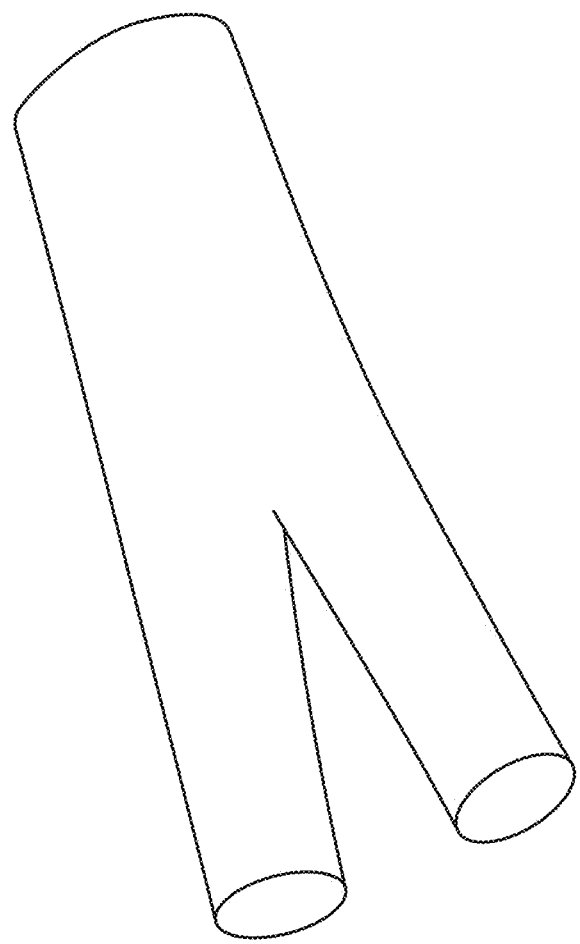
FIG. 9 shows a stainless bar that is inserted into the tubular fabric of large diameter portion in order to fix a heat setting mold.

In order to fix a heat setting mold, a stainless tube to be inserted into the tubular fabric of the large diameter portion had a cylindrical shape with a diameter of 25 mm and was slightly flattened at its end, and its branched portion had a cylindrical structure with a diameter of 12 mm. A stainless bar having the shape as shown in FIG. 9 was used in heat setting. For preparing a tubular woven fabric without wrinkles, it is preferred to appropriately change the shape or thickness of the end of the portion corresponding to the large diameter portion or the branched portion, according to the form of the woven texture of the boundary portion, or the desired density. Particularly, the stainless bar for the branched portion needs to be prepared by consideration of the decrease in the diameter of the tubular woven fabric caused by the single texture or the like.

The characteristics of the fabrics thus finished by these treatments (Examples 12 to 20) are as shown in Tables 3 and 4. These Examples were found to have an excellent thickness and burst strength, low water permeability at the normal base fabric sections, and low water permeability in the branched portion. The fabric having no single texture in fabric texture before and after the branching point (FIG. 5) had high water permeability, including the branching point, due to an aperture generated in the branching point.

(Scouring Condition)

Stirring and rinsing for 1 hour in an aqueous sodium carbonate solution (concentration: 5 g/l) of 90° C.

Stirring and rinsing for 30 minutes in ultrapure water of 90° C., repeated 3 times Length fixation and drying in the biaxial direction at room temperature (Heat Setting Condition)

A woven fabric after scouring and drying was inserted to a φ50 mm×200 mm long stainless mandrel preheated to 180° C. in a thermostat bath. Both ends of the 200 mm long woven fabric were fixed without wrinkles and looseness using a hose band.

The woven fabric-fixed stainless mandrel was introduced to a thermostat bath of 180° C. and heat set for 20 minutes from the point in time when the internal temperature of the thermostat bath was controlled to 180° C.

(Sterilization Condition)

Heat treatment is performed for 30 minutes in a thermostat bath of 185° C.

TABLE 3

| | | Warp yarn | | Weft yarn | | Twist | | | | | | |
| | | Removed yarn Total | | Removed yarn Total | | number (T/m) | | Twist coefficient | | Warp/weft twist | Weft yarn | Warp yarn |
| | Yarn type | fineness/single filament fineness | Yarn type | fineness/single filament fineness | Warp yarn | Weft yarn | Warp yarn | Weft yarn | coefficient ratio B | tension (cN/dtex) | tension (cN/dtex) |
| --- | --- | --- | --- | --- | --- | --- | --- | --- | --- | --- | --- |
| Example 12 | PET | 36.0/1.5 | PET | 26.0/0.17 | 500 | 100 | 3000 | 510 | 5.9 | 0.2 | 0.9 |
| Example 13 | PET | 36.0/1.5 | PET | 26.0/0.17 | 500 | 100 | 3000 | 510 | 5.9 | 0.2 | 0.9 |
| Example 14 | PET | 36.0/1.5 | PET | 26.0/0.17 | 500 | 100 | 3000 | 510 | 5.9 | 0.2 | 0.9 |
| Example 15 | PET | 36.0/1.5 | PET | 36.0/0.46 | 500 | 100 | 3000 | 600 | 5.0 | 0.2 | 0.9 |
| Example 16 | PET | 36.0/1.5 | PET | 36.0/0.46 | 500 | 100 | 3000 | 600 | 5.0 | 0.2 | 0.9 |
| Example 17 | PET | 36.0/1.5 | PET | 36.0/0.46 | 500 | 100 | 3000 | 600 | 5.0 | 0.2 | 0.9 |
| Example 18 | PET | 36.0/1.5 | PET | 36.0/0.46 | 500 | 100 | 3000 | 600 | 5.0 | 0.2 | 0.9 |

TABLE 3-continued

| | | | | | | | | | | | |
|---|---|---|---|---|---|---|---|---|---|---|---|
| Example 19 | PET | 36.0/1.5 | PET | 48.0/0.46 | 500 | 100 | 3000 | 693 | 4.3 | 0.2 | 0.9 |
| Example 20 | PET | 27.0/0.18 | PET | 30.0/0.2 | 500 | 100 | 2598 | 548 | 4.7 | 0.2 | 0.9 |

| | Warp density (no./2.54 cm) | Weft density (no./2.54 cm) | Warp yarn cover factor CFw | Weft yarn cover factor CFw | Sum of warp yarn and weft yarn cover factors CFw + CFf | Superfine structure ratio (%) | Single weave portion of woven fabric | |
|---|---|---|---|---|---|---|---|---|
| | | | | | | | Woven texture | Number of warps (no.) |
| Example 12 | 214 | 174 | 1284 | 887 | 2171 | 37 | FIG. 6 | 24 |
| Example 13 | 214 | 174 | 1284 | 887 | 2171 | 37 | FIG. 7 | 20 |
| Example 14 | 214 | 174 | 1284 | 887 | 2171 | 37 | FIG. 8 | 20 |
| Example 15 | 180 | 168 | 1080 | 1008 | 2088 | 0 | FIG. 9 | 0 |
| Example 16 | 180 | 168 | 1080 | 1008 | 2088 | 0 | FIG. 6 | 24 |
| Example 17 | 180 | 168 | 1080 | 1008 | 2088 | 0 | (Reference FIG. 6) | 4 |
| Example 18 | 180 | 168 | 1080 | 1008 | 2088 | 0 | (Reference FIG. 6) | 44 |
| Example 19 | 180 | 146 | 1080 | 1012 | 2092 | 0 | FIG. 6 | 24 |
| Example 20 | 208 | 192 | 1081 | 1052 | 2132 | 50.6 | FIG. 6 | 24 |

TABLE 4

| | Degree of yarn overlap | | Ratio of horizontal diameter to vertical diameter Dh/Dv | | Intra-yarn single filament fineness ratio S | | Warp/weft single filament fineness | | Warp yarn crimp ratio Dw/Df | angleθ (degree) | Thickness (μm) | Burst strength (N) | Tear force (N) | Water permeability Before needle puncture |
|---|---|---|---|---|---|---|---|---|---|---|---|---|---|---|
| | Warp yarn | Weft yarn | Warp yarn | Weft yarn | Warp yarn | Weft yarn | Warp yarn | Weft yarn | | | | | | |
| Example 12 | 0.9 | 1.1 | 2.5 | 5.4 | 1.1 | 1.1 | 9 | 12 | 74 | 215 | 4.3 | 113 | | |
| Example 13 | 0.9 | 1.1 | 2.5 | 5.4 | 1.1 | 1.1 | 9 | 12 | 74 | 215 | 4.3 | 113 | | |
| Example 14 | 0.9 | 1.1 | 2.5 | 5.4 | 1.1 | 1.1 | 9 | 12 | 74 | 215 | 4.3 | 113 | | |
| Example 15 | 0.9 | 1.0 | 2.4 | 5.6 | 1.1 | 1.2 | 3 | 12 | 74 | 215 | 5.4 | 142 | | |
| Example 16 | 0.9 | 1.0 | 2.4 | 5.6 | 1.1 | 1.2 | 3 | 12 | 74 | 215 | 5.4 | 142 | | |
| Example 17 | 0.9 | 1.0 | 2.4 | 5.6 | 1.1 | 1.2 | 3 | 12 | 74 | 215 | 5.4 | 142 | | |
| Example 18 | 0.9 | 1.0 | 2.4 | 5.6 | 1.1 | 1.2 | 3 | 12 | 74 | 215 | 5.4 | 142 | | |
| Example 19 | 0.9 | 1.1 | 2.9 | 5.2 | 1.4 | 1.1 | 3 | 13 | 84 | 244 | 6.1 | 149 | | |
| Example 20 | 0.9 | 1.1 | 2.3 | 5.1 | 1.3 | 1.2 | 1 | 11 | 66 | 194 | 4.0 | 105 | | |

| | Water permeability After needle puncture | Water permeability including boundary portion (l/min) | Porosity of warp yarn (%) | Porosity of weft yarn (%) | Crimp percentage of warp yarn (%) | Crimp percentage of weft yarn (%) | Catheter insertability (6 mm hole) |
|---|---|---|---|---|---|---|---|
| Example 12 | 142 | 4.1 | 17 | 48 | 1.6 | 12.5 | A |
| Example 13 | 142 | 4.9 | 17 | 48 | 1.6 | 12.5 | A |
| Example 14 | 142 | 5.2 | 17 | 48 | 1.6 | 12.5 | A |
| Example 15 | 208 | 18.5 | 18 | 22 | 3.3 | 6.0 | A |
| Example 16 | 208 | 7.3 | 18 | 22 | 3.3 | 6.0 | A |
| Example 17 | 208 | 11.6 | 18 | 22 | 3.3 | 6.0 | A |
| Example 18 | 208 | 5 | 18 | 22 | 3.3 | 6.0 | A/B |
| Example 19 | 212 | 8.1 | 18 | 21 | 4.1 | 5.2 | A/B |
| Example 20 | 123 | 3.7 | 33 | 39 | 3.4 | 10.1 | A |

INDUSTRIAL APPLICABILITY

The medical fabric of the present invention is suitably applicable as a material for implantation into the human body, including artificial blood vessels, artificial fiber fabrics for use in inguinal hernia treatments, etc., antiadhesive agents, prosthetic ligaments, artificial valves, and the like, and also suitably applicable as an in vitro material for medical use such as a hemofiltration material, a cell separating membrane, a cell adsorption material, or a cell culturing substrate, in addition to the material for implantation into the human body. A tubular seamless fabric comprising the medical fabric of the present invention allows a stent graft to have a low profile, which can therefore reduce the physical and economical burdens on patients in such a way as to shorten the inpatient periods, and can also reduce risks such as vascular wall damage. Furthermore, the provision of the tubular seamless fabric can widen the range of applications even to cases that have hitherto been excluded as targets of transcatheter intravascular treatment, such as females and Asians that have narrower arteries.

EXPLANATIONS OF REFERENCE SYMBOLS

1: Weft yarn
2: Warp yarn
X1: Width of an arbitrary yarn cross section
X2: Width of a yarn cross section adjacent to X1
Y: Width from X1 to X2
Dh: Diameter in the horizontal direction on the weft yarn cross section
Dv: Diameter in the vertical direction on the weft yarn cross section
Z1: Horizontal line traversing adjacent wefts
Z2: Inclined line of warp yarn
θ: Warp yarn crimp angle

The invention claimed is:

1. A medical fabric comprising multifilament yarns with a total fineness of 7 to 80 dtex as warp yarns and weft yarns, wherein a single filament fineness of at least one multifilament yarn among the warp yarns and the weft yarns is 0.5 dtex or less, a twist coefficient A of the weft yarns is 50 to 1000, a thickness of the medical fabric is 10 to 90 μm, a water permeability before and after needle puncture of the medical fabric is 300 cc/min/cm$^2$ or less, a twist coefficient of the warp yarns is 75 to 10000, and a warp/weft twist coefficient ratio B between the warp yarns and the weft yarns is 3.6 to 20.

2. The medical fabric according to claim 1, wherein a degree of weft yarn overlap (WW) of the weft yarns is 1.0 to 1.5.

3. The medical fabric according to claim 1, wherein a warp yarn crimp angle of the warp yarns is 20 degrees or smaller.

4. The medical fabric according to claim 1, wherein intra-yarn single filament fineness ratios S for both the warp yarns and the weft yarns are 2 or less.

5. The medical fabric according to claim 1, wherein a ratio of a diameter in the horizontal direction (Dh) to a diameter in the vertical direction (Dv) in the weft yarn cross section of the woven fabric is 1.5<Dh/Dv<10.

6. The medical fabric according to claim 1, wherein a sum of a cover factor (CFw) of the warp yarns and a cover factor (CFf) of the weft yarns (CFw+CFf) is 1600 to 2400.

7. A tubular seamless fabric comprising a medical fabric according to claim 1.

8. A stent graft comprising the tubular seamless fabric according to claim 7.

9. A catheter in which a stent graft according to claim 8 is inserted.

10. A stent delivery device comprising a stent graft according to claim 8 as a component thereof.

11. The tubular seamless fabric according to claim 7, wherein the tubular seamless fabric has a large diameter portion and a branched portion, wherein partial fabric texture at a boundary portion between the large diameter portion and the branched portion is constituted by a single texture and has a burst strength of 100 N or larger.

12. The tubular seamless fabric according to claim 11, wherein a number of warps constituting the single texture is 2 to 32.

13. A method for producing a tubular seamless fabric according to claim 11, comprising the step of performing weaving in a loom provided with a shuttle having the weft yarns wound on a bobbin.

14. A stent graft comprising a medical fabric according to claim 1.

15. A catheter in which a stent graft according to claim 14 is inserted.

16. A stent delivery device comprising a stent graft according to claim 14 as a component thereof.

17. The medical fabric according to claim 1, wherein the warp/weft twist coefficient ratio B between the warp yarns and the weft yarns is 4.6 to 20.

18. The medical fabric according to claim 1, wherein the warp/weft twist coefficient ratio B between the warp yarns and the weft yarns is 5.2 to 20.

19. The medical fabric according to claim 1, wherein the warp/weft twist coefficient ratio B between the warp yarns and the weft yarns is 6.7 to 20.

20. A tubular seamless fabric comprising
a medical fabric including multifilament yarns with a total fineness of 7 to 80 dtex as warp yarns and weft yarns,
wherein a single filament fineness of at least one multifilament yarn among the warp yarns and the weft yarns is 0.5 dtex or less,
wherein a twist coefficient A of the weft yarns is 50 to 2000,
wherein a thickness of the medical fabric is 10 to 90 μm,
wherein a water permeability before and after needle puncture of the medical fabric is 300 cc/min/cm$^2$ or less,
wherein the tubular seamless fabric has a large diameter portion and a branched portion,
wherein partial fabric texture at a boundary portion between the large diameter portion and the branched portion is constituted by a single texture and has a burst strength of 100 N or larger, and
wherein a number of warps constituting the single texture is 2 to 32.

* * * * *